(12) United States Patent
Bats et al.

(10) Patent No.: US 8,903,662 B2
(45) Date of Patent: Dec. 2, 2014

(54) METHOD FOR DETERMINING THE HEATING VALUE AND THE RELATIVE DENSITY OF A HYDROCARBON FUEL AND APPARATUS FOR THE SAME

(75) Inventors: Johan Bats, Antwerp (BE); Floris J. J. Huijsmans, Tilburg (NL)

(73) Assignee: ANU-BIZ BVBA, Turnhout (BE)

( * ) Notice: Subject to any disclaimer, the term of this patent is extended or adjusted under 35 U.S.C. 154(b) by 889 days.

(21) Appl. No.: 12/741,026

(22) PCT Filed: Oct. 24, 2008

(86) PCT No.: PCT/IB2008/003237
§ 371 (c)(1),
(2), (4) Date: Dec. 14, 2010

(87) PCT Pub. No.: WO2009/063315
PCT Pub. Date: May 22, 2009

(65) Prior Publication Data
US 2011/0098936 A1 Apr. 28, 2011

(51) Int. Cl.
*G01N 9/36* (2006.01)
*G01N 33/00* (2006.01)
(Continued)

(52) U.S. Cl.
CPC .............. *G01N 33/225* (2013.01); *G06F 19/00* (2013.01); *G06F 17/40* (2013.01); *G01N 9/36*
(Continued)

(58) Field of Classification Search
CPC .............. F23N 1/00; F23N 1/02; F23N 3/00; F23N 5/00; F23N 2005/00; F23N 2023/02; F23N 2025/00; D01D 21/00; G01F 1/00; G01F 1/74; G01K 17/00; G01K 17/02; G01K 17/04; G01K 17/06; G01N 9/00; G01N 9/36; G01N 33/00; G01N 33/004; G01N 33/22; G01N 33/225; G06F 11/00; G06F 11/30; G06F 11/32; G06F 17/00; G06F 17/40; G06F 19/00; G01D 21/00
USPC ........... 44/903; 73/32 R, 53.01, 61.41, 64.44, 73/64.54, 432.1, 865.8, 865.9, 866.3; 340/500, 540; 374/31, 36, E17.001; 431/2, 12, 13; 700/1, 90, 266, 274; 701/1, 99, 101, 102, 103, 104; 702/1, 702/22, 23, 24, 30, 127, 137, 182, 187, 702/189; 708/100, 200
IPC ................ F23N 1/00,1/02, 3/00, 5/00, 2005/00, F23N 2023/02, 2025/00; G01D 21/00; G01F 1/00, 1/74; G01K 17/00, 17/02, 17/04, 17/06; G01N 9/00, 9/36, 33/00, 33/004, 33/22, 33/225; G06F 11/00, 11/30, 11/32, 17/00, 17/40, G06F 19/00
See application file for complete search history.

(56) References Cited

U.S. PATENT DOCUMENTS 2,702,590 A * 2/1955 Stillman ........................... 431/9
2,715,831 A * 8/1955 Catford et al. ................. 73/32 R
(Continued)

FOREIGN PATENT DOCUMENTS

EP          0560501 A2 *  9/1993
WO     WO 90/10222 A  *  9/1990
WO     WO 03/048692 A1 * 6/2003

OTHER PUBLICATIONS

ASTM Standard D-4891, entitled "Standard Test Method for Heating Value of Gases in Natural Gas Range by Stoichiometric Combustion", 2006.
(Continued)

*Primary Examiner* — Edward Cosimano
(74) *Attorney, Agent, or Firm* — Kimberly A. Chasteen

(57) ABSTRACT

There is disclosed a method for determining the heating value of a fuel, the fuel comprising at least one hydrocarbon including a first hydrocarbon present in the highest molar concentration, the method comprising: measuring the stoichiometric oxidation molar flow ratio of the fuel; determining the ideal molar heating value ($HV_{m,i}$) from the measured stoichiometric oxidation molar flow ratio; measuring the molar concentration of the first hydrocarbon; and determining the real molar heating value ($HV_{m,r}$) from the ideal molar heating value ($HV_{m,i}$) and the molar concentration of the first hydrocarbon. An apparatus is also disclosed.

32 Claims, 11 Drawing Sheets

(51) Int. Cl.
  *G01K 17/02* (2006.01)
  *G01F 1/74* (2006.01)
  *G06F 19/00* (2011.01)
  *G06F 17/40* (2006.01)
  *G01N 33/22* (2006.01)

(52) U.S. Cl.
  CPC ......... (2013.01); *G01F 1/74* (2013.01); *G01K 17/02* (2013.01); *G01N 33/0004* (2013.01); *Y10S 44/903* (2013.01)
  USPC ............... 702/24; 44/903; 73/32 R; 73/61.41; 73/64.44; 73/64.54; 73/865.8; 374/36; 431/13; 702/1; 702/23; 702/127; 702/182; 702/187; 702/189

(56) References Cited

U.S. PATENT DOCUMENTS

| | | | |
|---|---|---|---|
| 2,752,989 A * | 7/1956 | Jenkins, Jr. | 431/157 |
| 2,780,414 A * | 2/1957 | De Heer | 431/12 |
| 2,866,602 A * | 12/1958 | Dailey, Jr. et al. | 236/15 R |
| 3,072,468 A * | 1/1963 | Stitzer | 48/180.1 |
| 3,193,357 A * | 7/1965 | Benzinger | 436/174 |
| 3,211,531 A * | 10/1965 | Benzinger | 422/51 |
| 3,388,862 A * | 6/1968 | Gabrielson | 431/8 |
| 3,982,878 A * | 9/1976 | Yamane et al. | 431/2 |
| 4,118,172 A * | 10/1978 | Noir et al. | 431/12 |
| 4,204,830 A * | 5/1980 | Jones et al. | 431/8 |
| 4,306,451 A * | 12/1981 | Szonntagh | 374/36 |
| 4,315,430 A * | 2/1982 | Szonntagh | 374/37 |
| 4,386,858 A * | 6/1983 | Kude et al. | 374/37 |
| 5,224,776 A * | 7/1993 | Clingman et al. | 374/36 |
| 5,288,149 A * | 2/1994 | Meyer | 374/36 |
| 5,759,862 A * | 6/1998 | Vander Heyden et al. | 436/147 |

OTHER PUBLICATIONS

British Standard BS 4250: 1997, entitled "Specification for commercial butane and commercial propane".
GPA 2172, 1996.
AGA Report No. 10—Speed of Sound in Natural Gas and Other Related Hydrocarbon Gases (American Gas Association 2003).
AGA-8, 1992.
ISO 6976, 1995.

* cited by examiner

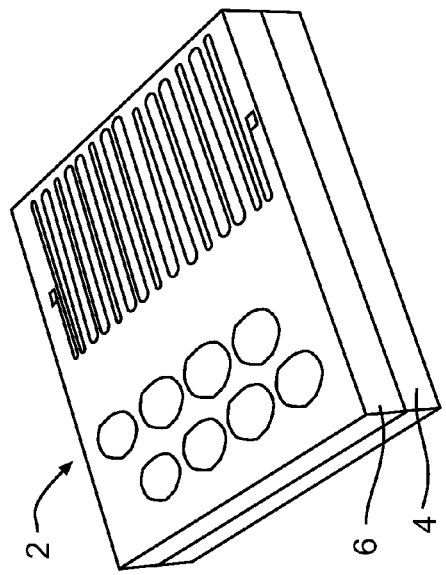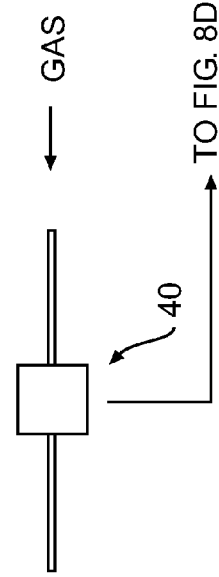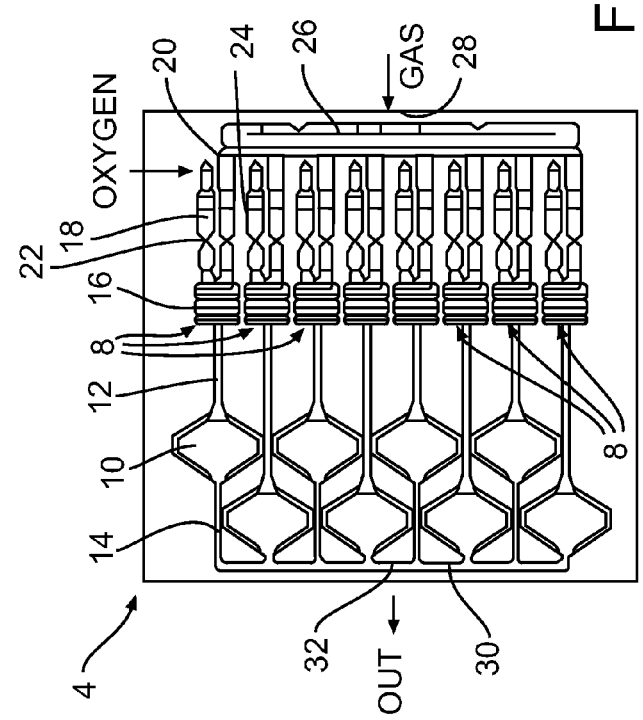

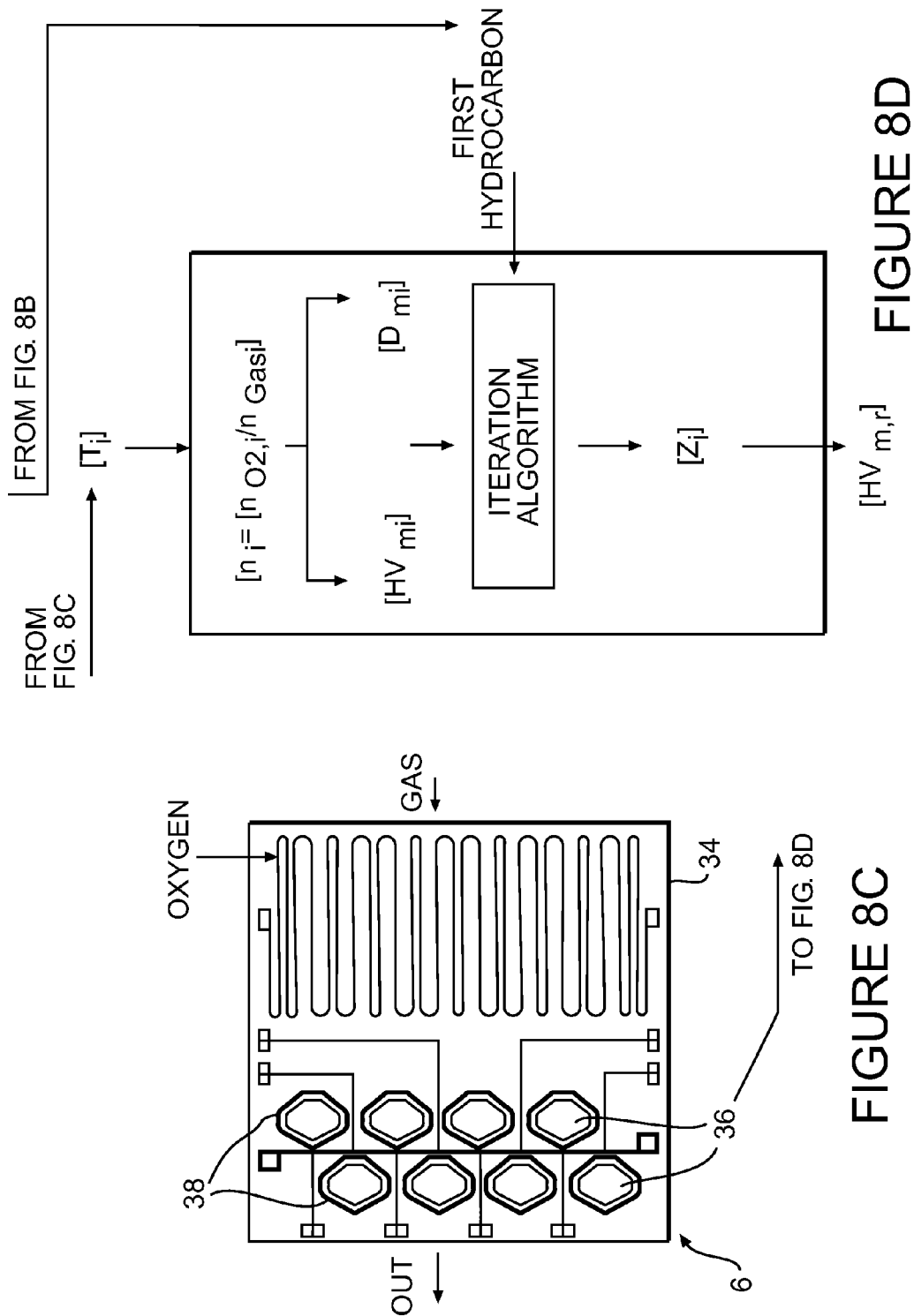

METHOD FOR DETERMINING THE HEATING VALUE AND THE RELATIVE DENSITY OF A HYDROCARBON FUEL AND APPARATUS FOR THE SAME

CROSS REFERENCE TO RELATED APPLICATION

The present application claims priority from PCT Patent Application No. PCT/IB2008/003237 filed 24 Oct. 2008 and GB Patent Application GB0721329.1 filed 31 Oct. 2007.

BACKGROUND OF THE INVENTION

The present invention relates to a method and apparatus for determining the heating value and the relative density (or specific gravity) of a hydrocarbon fuel. These values are used to define the energy content and/or the Wobbe Index of a hydrocarbon fuel.

Contracts for the supply of hydrocarbon fuels are based upon the average values of the energy content of the gas on an hourly or daily basis. Accordingly, the primary concern of designers or equipment for the measurement of the energy content of fuels has been on the accuracy of the measurements. The most commonly used instrument today to measure the energy content of fuel gases for industrial use, is the process gas chromatograph (PGC). This instrument, sometimes referred to as 'BTU analyser', is characterised by having a high accuracy, but also a long analysis time, of the order of several minutes, typically from 3 to 5 minutes. Further, the instrument is complex to construct, operate and maintain and requires multi-component gases in order to calibrate. These factors provide the need for an improved means for measuring the energy content of a fuel that is both fast and accurate, while being simple to construct, operate and maintain.

The Wobbe Index is a calculated value used to provide a comparison of the combustion energy output of different fuel streams, in particular gaseous fuels. By comparing the Wobbe Index of different fuels, an indication of their different energy outputs during combustion can be obtained. Thus, two fuels of different composition having a similar Wobbe Index will provide a similar energy output when combusted under a given set of conditions.

The Wobbe Index (WI) is calculated from the heating value (HV) and the relative density (RD) of a fuel and is defined by the following formula:

$$WI = HV/\sqrt{RD}.$$

The Wobbe Index is used on a commercial scale to compare the combustion energy output of different hydrocarbon fuels, in particular hydrocarbon fuel gases. Accordingly, the accurate determination of the Wobbe Index is important for a wide range of industries, most notably the natural gas industry.

There is a particular need for a means of determining the Wobbe Index that is both fast and accurate for application in fuel burner installations, especially gas burner installations. This need arises as a result of safety and environmental issues in connection with the operation of the burner installation. Such an improved means for determining the Wobbe Index would also be of considerable use in fuel mixing stations, where a fast analysis time is required in order to reduce the internal volume of the buffer lines employed in the fuel supply system.

Fast meters for determining the energy and/or the Wobbe Index are known. A first type is based on the requirements of ASTM Standard D-4891, entitled 'Standard Test Method for Heating Value of Gases in Natural Gas Range by Stoichiometric Combustion'. D-4891 concerns the determination of the heating values of gases within a certain composition range. The method is based upon the linear relationship between the heating value of natural gas and the stoichiometric gas oxidation flow disclosed in the standard. The fuel is combusted with oxygen (or air) and either the temperature of the combustion or the oxygen (or air) flow rate at the outlet is measured in order to determine the stoichiometric oxidation gas flow conditions. The method disclosed in D-4891 is fast, having a response time of less than 15 seconds, and is relatively accurate, with an accuracy of about 0.4%. The method also has the advantage that it can be applied to a wide range of gas compositions without the need for extensive and time consuming recalibration. However, in order to determine the Wobbe Index, the method of D-4891 must be combined with a method for measuring the density of the fuel gas having the same level of accuracy and speed of response.

A second type of fast meter for determining the energy content and/or the Wobbe Index of a fuel is applied to the measurement of so-called generic fuel gases, that is natural gas produced as a result of hydrocarbon exploration and production activities. The composition of generic natural gases is assumed to consist of four dependent components: nitrogen ($N_2$), carbon dioxide ($CO_2$), methane ($CH_4$) and the so-called 'equivalent hydrocarbon' (CH). The equivalent hydrocarbon represents the higher hydrocarbons of the gas, which are assumed to consist essentially of alkanes. According to the one third rule generally applicable to generic gases, the molar ratio of consecutive higher hydrocarbons is about one third, that is, for example, the molar ratio of propane to ethane is about ⅓, the molar ratio of propane to butane in the gas is about ⅓, and so on. These characteristics allow generic natural gases to be characterised using three independent properties of the gas, referred to as the 'correlative principle for generic natural gases'. Meters for the determination of the energy content and/or the Wobbe Index for generic natural gases operating on the principle of the one third rule are referred to as "Correlative Meters" and apply the measurement of three independent properties. Examples of suitable independent properties include the heating value of the gas, the density of the gas, the velocity of sound in the gas, the heat capacity of the gas, the heat conductivity of the gas and the concentration of carbon dioxide. Such meters are characterised by combining a fast response time, typically less than 15 seconds, with an acceptable accuracy of measurement of both the heating value and density of the gas, typically within 0.5%. However, as a result of the principles on which these meters operate, in particular the equivalent hydrocarbon theory and the one third rule, their application is limited to naturally produced fuel gases. Correlative meters cannot be applied to other fuel gases, such as natural gas that has been treated, for example to strip propane and butane, or blended with nitrogen, and other fuel gases, such as biogas, refinery gases and the like, since such fuels do not have a composition that follows the one third rule.

Accordingly, there is a need for a means for determining the energy and/or the Wobbe Index of a wide range of fuels, not just natural gases, that combines a high speed of response and a high degree of accuracy. It would also be advantageous if such means could be simple to construct and operate, requiring little or no calibration and little or no maintenance.

SUMMARY OF THE INVENTION

In a first aspect, the present invention provides a method for determining the heating value of a fuel, the fuel comprising at least one hydrocarbon including a first hydrocarbon present in the highest molar concentration, the method comprising:

measuring the stoichiometric oxidation molar flow ratio of the fuel;

determining the ideal molar heating value ($HV_{m,i}$) from the measured stoichiometric oxidation molar flow ratio;

measuring the molar concentration of the first hydrocarbon; and determining the real molar heating value ($HV_{m,r}$) from the ideal molar heating value ($HV_{m,i}$) and the molar concentration of the first hydrocarbon.

The ideal molar heating value ($HV_{m,r}$) is in linear relationship with the stoichiometric oxygen (or air) fuel ratio, from which the $HV_{m,i}$ can be determined in known manner. However, it has been found that the real molar heating value ($HV_{m,r}$) deviates from the $HV_{m,i}$ by a significant amount. This in turn limits the accuracy of the determination of the $HV_{m,r}$ using the known techniques to about ±0.40%. Accordingly, operations, such as the operation of a fuel combustion installation, based upon the $HV_{m,i}$ will be inaccurate, leading to inefficient use of the fuel. In the method of the first aspect of the present invention, the $HV_{m,r}$ is determined from the in combination with a correction based upon the hydrocarbon composition of the fuel. In this way, it has been found possible to determine the $HV_{m,i}$ to an accuracy of as high as ±0.05% for a very wide range of natural gases, and as high as ±0.10% for a very wide range of liquefied petroleum gas (LPG) fuels.

The method of the present invention may be applied to a wide range of hydrocarbon fuels, including both gaseous and liquid fuels, albeit that liquid fuels have to be vaporised before injection into the measurement device. In practice, the measurement of the heating value and Wobbe Index of hydrocarbon fuels will be limited by the boiling point and the viscosity of the fuel. This means that the practical use of the method is limited to below the heating oil distillate fraction of crude oil (boiling point between 200-350° C., length of hydrocarbon chain $C_{15}$-$C_{18}$). Higher crude-derived hydrocarbon fractions, for example lubricating oil, asphalt, and residues, are rarely used as fuels for heating or combustions applications. In practice, it would be technically difficult to measure their heating value and Wobbe Index using the method of the present invention, due to the need to vapourise the hydrocarbons. Therefore the method of the present invention is generally more applicable to liquid fuels in the lighter crude fraction (sometimes referred to as Class A), with fractionation products such as liquefied petroleum gas (LPG), gasoline, and light fuel oils such as diesel, kerosene, jet fuels and heating oil.

The method of this aspect of the present invention is particularly suitable for determining the molar heating value of gaseous fuels. It is an advantage of the method that it may be applied to a wide range of gaseous fuel compositions, including generic natural gas as well as other fuel gases, such as refinery gas, treated natural gas, synthetic natural gas (SNG), biogas and the like. In other words, the method of the present invention may be applied to both generic and non-generic fuels, that is fuels that do not follow the one third rule.

As noted, the method of the present invention requires the identification of the first hydrocarbon component, that is the hydrocarbon component present in the fuel in the highest molar concentration and the measurement of that concentration. As also noted, in the case of a generic or treated natural gas, this component is methane. The molar composition of the natural gases commercially distributed worldwide generally varies within the following ranges:

| | |
|---|---|
| Nitrogen | 0-20% |
| Methane | 60-100.0% |
| $CO_2$ | 0-15% |
| Ethane | 0-15% |
| Propane | 0-6% |
| Butanes | 0-1.5% |
| Pentanes | 0-1% |
| $C_{6+}$ | 0-0.2%. |

In the case of other fuels, the first hydrocarbon component may be a higher hydrocarbon, for example ethane, propane or butane, etc. In the case of LPG, the hydrocarbon molar composition will be different for 'Propane'-LPG and 'Butane'-LPG. British Standard BS 4250: 1997, entitled 'Specification for commercial butane and commercial propane' specifies the following maxima for the component concentrations (ignoring trace components such as sulphur and ammonia, which are not shown, since they are of no influence on the heating value or the Wobbe Index of the LPG) for these fuels:

| | 'Propane'-LPG | 'Butane'-LPG |
|---|---|---|
| Ethylene | 1% | 0% |
| Acetylene | 0.5% | 0.5% |
| Propane | balance | 0% |
| Propylene | 0.5% | 0.5% |
| Butanes | 10% | balance |
| Butylene | 0.1% | 0.1% |
| Pentanes | 2% | 2%. |

In the method of the present invention, in the case of LPG, the first hydrocarbon is propane or butane, depending upon the type of LPG under consideration, whichever of these components is the hydrocarbon present in the highest molar concentration, and the molar concentration of propane or butane is measured for use in determining the $HV_{m,r}$.

In practice, if the concentration of the first hydrocarbon in the fuel is to be measured using a single component measurement device, the measurement device will be limited in its application to analysis of fuels having this component as the first hydrocarbon. Thus, for example, a device employing a single infrared (IR) detector with a bandwidth dedicated to a given hydrocarbon, will be specific to hydrocarbon fuels having this given hydrocarbon as the first hydrocarbon. Alternatively, the measurement device may be operable to measure the concentration of more than one hydrocarbon. For example, a device may comprise a plurality of IR detectors, each having a bandwidth dedicated to a different hydrocarbon. In this way, the measurement device may be made applicable to a wider range of fuels.

The method of the first aspect of the present invention is applied to fuels comprising at least one hydrocarbon. The fuel may comprise a single hydrocarbon, for example methane in the case of a natural gas, either alone or in combination with one or more other, non-hydrocarbon components, for example nitrogen and/or carbon dioxide. More typically, the fuel comprises a mixture of a plurality of hydrocarbons. Thus, in the case of a natural gas, the fuel will comprise methane as the predominant hydrocarbon, with lesser concentrations of higher hydrocarbons, together with one or more non-hydrocarbon components, in particular nitrogen and carbon dioxide. After the application range for the device is defined, the component present in the highest molar concentration is determined in known manner. Examples of possible application ranges with their dominant hydrocarbon component are as follows:

Natural gas, biogas, CNG and SNG (methane)

LPG (propane or butane)

Liquid Fuels (higher alkanes, typically octane).

The correction of the $HV_{m,i}$ is based upon the determination of the molar concentration of the hydrocarbon component that is present in the highest concentration.

In the case of a natural gas, be it generic or treated, the hydrocarbon component present in the highest molar concentration is methane. Accordingly, in the case of a natural gas, the $HV_{m,i}$ is determined from the linear relationship between the stoichiometric oxidation molar flow ratio of the gas and the $HV_{m,i}$. The $HV_{m,i}$ is corrected using the measured concentration of methane, to yield the $HV_{m,r}$.

The stoichiometric oxidation molar flow ratio of the fuel may be determined using techniques known in the art. Combustion or oxidation of the fuel over a range of molar ratios of oxygen (or air) to fuel will yield a temperature profile exhibiting a maximum or peak temperature at the stoichiometric ratio of oxygen (or air) and fuel. Referring to FIG. 1, there is shown a graph of the ratio of molar flow rate of oxygen (or air) to molar flow rate of fuel versus the temperature of oxidation for a given natural gas. As will be seen, the temperature of combustion varies with the molar ratio of oxygen (or air) to fuel, with all other combustion parameters being kept constant. The temperature profile exhibits a clear peak corresponding to the stoichiometric oxidation fuel ratio. In the case of the gas exemplified in FIG. 1, this ratio is 2.0.

It is preferred that the peak temperature measurement is determined with an accuracy of at least ±0.5° C., more preferably at least ±0.1° C.

Other methods of determining the stoichiometric oxidation flow ratio include the continuous measurement of the oxygen (or air) concentration at the outlet of the combustion chamber. By variation of the oxygen (or air)/gas flow ratio from lean to rich conditions, the oxygen (or air) depletion point can be defined, which point corresponds to the stoichiometric flow ratio.

The ideal molar heating value $HV_{m,i}$ is determined from the stoichiometric oxidation molar flow ratio. This may be achieved using techniques known in the art. For example, as noted above, it is known that the $HV_{m,i}$ exhibits a linear relationship with the stoichiometric molar flow ratio. Referring to FIG. 2A, there is shown a graph of the stoichiometric oxidation molar flow ratio (molar flow rate of oxygen (or air)/molar flow rate of fuel) versus the ideal heating value $HV_{m,i}$ for a very large selection of random natural gas compositions with certain boundaries for each of the components.

For the natural gas range displayed in FIG. 2A, these boundaries are:

| | |
|---|---|
| Nitrogen | 0-20% |
| Methane | 60-100.0% |
| $CO_2$ | 0-15% |
| Ethane | 0-15% |
| Propane | 0-6% |
| Butanes | 0-1.5% |
| Pentanes | 0-1% |
| Hexanes | 0-0.2%. |

It can be seen that the linear relationship holds for these natural gas samples with a correlation factor $R^2$ of 0.999987. Accordingly, this relationship may be used in the method of the present invention to determine the $HV_{m,i}$.

It has also been found that a similar linear relationship between the ideal molar density ($D_{m,i}$) and the stoichiometric molar flow ratio also exists. In this respect, the correlation factor $R^2$ for the selection of random natural gas compositions referred to above is 0.9836. The relationship between the ideal molar density ($D_{m,i}$) and the stoichiometric molar flow ratio is shown in FIG. 2B.

The method of the present invention further comprises determining the molar concentration of the first hydrocarbon component, that is the hydrocarbon component present in the highest molar concentration. As noted above, in the case of a natural gas, the first hydrocarbon component is methane. However, the first hydrocarbon component may be another hydrocarbon, in particular a higher alkane, such as ethane, propane, or butane, depending upon the fuel.

Methods for measuring the molar concentration of the first hydrocarbon are known in the art. Suitable methods for determining the molar concentration of the first hydrocarbon include infrared measurement techniques know in the art, as mentioned above. The non-dispersive infrared (NDIR) technique consists of measuring the component absorption of infrared light at a specific wavelength in the infrared region. The fundamental vibrational modes of the hydrocarbon components in hydrocarbon fuels are situated in the mid-infrared wavelength spectrum. By selection of the appropriate filter for the incident infrared light, corresponding to the resonant vibrational frequency of the component of interest, the concentration of this component can be measured in a relatively fast and accurate manner.

Other techniques for measuring the molar concentration of the first hydrocarbon are also known in the art and will be apparent to the person skilled in the art. For example, the light absorption technique could also be applied at other wavelengths, such as Near Infrared (NIR, 700-2500 nm) and Far Infrared (FIR, 25-1000 µm), although the light absorption of hydrocarbons is not as pronounced as in the mid infrared area. For hydrocarbons, absorption in the FIR region is due to changes in the rotational energy of the molecules, while absorption in the NIR domain is due to harmonics of the vibrational energy frequencies. In some cases the absorption might be less influenced by interference of absorption spectra of other molecules in the fuel at these wavelengths, in which case special care must be taken to compensate for the loss in signal strength.

Another technique for measuring individual hydrocarbon concentrations in fuels for use in the method of the present invention is gas chromatography, where the individual components are separated from each other in a separation column, based on the solubility differences of the components in the stationary phase of the column, and individually measured by a detector at the outlet of the column, such as a Thermal Conductivity Detector or a Flame Ionisation Detector. A further technique for measuring individual hydrocarbon concentrations in fuels is mass spectroscopy, where the components are ionised and separated from each other in a electro-magnetic field, of which the value is set such that all components are deflected from the detector path with the exception of the component of interest.

It is preferred that the molar concentration of the first hydrocarbon is determined to an accuracy of at least ±2% Full Scale, more preferably greater than ±1% Full Scale.

As described hereinbefore, the real molar heating value $HV_{m,r}$ is determined from the ideal molar heating value $HV_{m,i}$ and the molar concentration determined for the first hydrocarbon. As already noted, the $HV_{m,r}$ can deviate from the $HV_{m,i}$ by a significant amount. FIG. 3 shows the deviation of the $HV_{m,r}$ from the $HV_{m,i}$ for a large number of typical natural gas compositions. As can be seen, this deviation is ±0.4%, depending upon the gas composition. This error arises as a result of the compressibility Z of the components of the fuel. However, the correlation factor for the relationship between the $HV_{m,r}$ and the compressibility factor Z is poor and cannot be used to determine the $HV_{m,r}$ from the $HV_{m,i}$ with sufficient accuracy.

It has now been found that the deviation of the $HV_{m,r}$ from the $HV_{m,i}$ for a wide range of fuels correlates very closely with the variation in the concentration of the first hydrocarbon in the fuel. Referring to FIG. 4, there is shown a graph of the deviation of the $HV_{m,r}$ from the $HV_{m,i}$ against the molar stoichiometric oxidation flow ratio for a range of natural gas fuels commercially distributed on a worldwide scale. Referring to FIG. 5, there is shown a similar plot to that of FIG. 4 of the molar concentration of methane against the stoichiometric oxidation flow ratio for the same natural gas fuels. As can be seen, the deviation of the $HV_{m,r}$ from the $HV_{m,i}$ for the fuels correlates very well with the molar concentration of the first hydrocarbon, that is methane in the natural gas fuels. The same correlation holds for fuels with a first hydrocarbon other than methane, such as the fuels mentioned above.

The $HV_{m,r}$ is determined from the $HV_{m,i}$ and the molar concentration of the first hydrocarbon. The method of determining the is as follows:

1. Measure the stoichiometric oxidation flow and the concentration of the first hydrocarbon in the fuel;
2. Determine the correlation factor $R^2$ between $HV_{m,i}$ and the stoichiometric oxidation molar flow ratio for the range of fuels which are to be measured, as discussed hereinbefore and shown in FIG. 2A;
3. Measure the ideal molar density $(D_{m,i})$ for the fuel to be measured;
4. Determine the correlation factor $R^2$ between the ideal molar density $(D_{m,i})$ and the stoichiometric oxidation molar flow ratio for the range of fuels to be measured;
5. Define a start composition of the fuel which needs to be measured, with the measured concentration of the first hydrocarbon as a fixed value;
6. Calculate the $HV_{m,i}$ and $D_{m,i}$ using known methods (for example those defined in ISO 6976 or GPA 2172);
7. Vary the concentration of each component in the start composition in turn, by a small increment to provide a new composition;
8. Calculate the $HV_{m,i}$ and $D_{m,i}$ for the new composition using known methods.
9. Compare the values of $HV_{m,i}$ and $D_{m,i}$ calculated with those derived from the correlation curves with the stoichiometric oxidation molar flow ratio using the correlation factors $R^2$ for each;
10. If the difference in the value of $HV_{m,i}$ between that calculated using the composition and that determined using the correlation factors $R^2$ is less than 0.01%, use the composition to calculate the compressibility of the fuel. If not, repeat steps 7 to 9;
11. Calculate $HV_{m,r}$ by dividing the value of $HV_{m,i}$ for the final composition as obtained from the stoichiometric oxidation molar flow ratio using the correlation factors $R^2$ by the compressibility.

In the method set out above, in step 7, only compositional changes are taken into account which lead to values for $HV_{m,i}$ and $D_{m,i}$ which differ less than 0.1% and 0.5% respectively from the corresponding values calculated from the stoichiometric oxidation molar flow ratio using the correlation curves and factors $R^2$.

As an example of the determination of the $HV_{m,r}$, reference is made to FIG. 6, showing a graph of the calculation of the $HV_{m,r}$ from the $HV_{m,i}$ for a very wide range of gaseous fuel compositions, represented in terms of their molar stoichiometric oxidation flow ratios. As can be seen, the method of the present invention allows the real molar heating value the $HV_{m,r}$ to be determined with an accuracy of ±0.05%.

In a second aspect, the present invention provides an apparatus for determining the heating value of a fuel, the fuel comprising at least one hydrocarbon including a first hydrocarbon present in the highest molar concentration, the apparatus comprising:

means for measuring the stoichiometric oxidation molar flow ratio of the fuel; means for determining the ideal molar heating value $(HV_{m,i})$ from the measured stoichiometric oxidation molar flow ratio;

means for measuring the molar concentration of the first hydrocarbon; and means for determining the real molar heating value $(HV_{m,r})$ from the ideal molar heating value $(HV_{m,i})$ and the molar concentration of the first hydrocarbon.

The means for measuring the stoichiometric oxidation molar flow ratio of the fuel and the means for measuring the molar concentration of the first hydrocarbon may be any suitable means for implementing the techniques discussed hereinbefore.

The means for determining the ideal and real molar heating values, $HV_{m,i}$ and $HV_{m,r}$, may be any suitable processor or computer. Suitable processors will be known to the person skilled in the art and are available commercially.

As described above, the determination of the Wobbe Index for a fuel requires a calculation of the real molar heating value $HV_{m,r}$ and the relative density or specific gravity of the gas. It follows that an accurate calculation of the Wobbe Index requires an accurate determination of both the $HV_{m,r}$ and the relative density.

In a further aspect, the present invention provides a method of determining the relative density of a fuel comprising at least one hydrocarbon component, the method comprising:

determining the real heating value of the fuel;

measuring the velocity of sound of the fuel;

measuring the concentration of carbon dioxide in the fuel; and determining the relative density of the fuel from the real heating value, the velocity of sound and the concentration of carbon dioxide.

The method of this aspect of the invention may be applied to a wide range of hydrocarbon fuels, including both liquid and gaseous fuels, as described hereinbefore. The method is particularly advantageous in the determination of the relative density of a gaseous fuel, in particular a generic or treated natural gas, refinery gas, fuel gas, biogas, SNG (synthetic natural gas) or the like.

The method of determining the relative density requires a determination of the real heating value of the fuel. Any suitable method may be employed. However, it is particularly preferred to employ the method of determining the $HV_{m,r}$ of the first aspect of the present invention and described hereinbefore.

The velocity of sound in the fuel may be determined using any technique known in the art. If the method is being applied to a liquid fuel, the fuel must first be vaporised, as described hereinbefore. Generally, the measurement of the velocity of sound in the fuel requires that the pressure upstream of the apparatus carrying out the measurement of the speed of sound is known. The downstream pressure of the fuel is typically ambient or close to ambient pressure. Fluctuations in the downstream pressure will not adversely affect the method, provided that the pressure drop of the fuel flowing through the apparatus is such that sonic conditions are valid, that is the pressure downstream is less than 0.52 times the pressure of the fuel upstream of the measuring.

Suitable techniques for measuring the velocity of sound in the gaseous fuel are known in the art and will be apparent to the person skilled in the art. One suitable technique to measure the velocity of sound is the actual measurement of the flow in the throat of a sonic nozzle, with upstream and downstream pressure settings such that sonic conditions are created in the throat of the sonic nozzle. A flow sensor, by preference a thin film metal sensor, is installed in the throat of the orifices. Noble metals such as gold, platinum, rhodium, iridium or palladium are preferred. The sensor is electronically embedded in a 4-wire configuration: one pair serves for the heater current through the sensor, the other pair for the measurement current. Upstream and downstream temperature sensors are used to measure the temperature difference before and after the throat section, which is proportional to the actual velocity of sound. A second set of sensors is required to take measurements of the velocity of sound at a second set of conditions, in order compensate for the influence of density, viscosity and heat capacity of the fuel being measured. This can be done in a parallel channel under the same pressure conditions, but with different ambient temperature settings, or in the same channel upstream or downstream of the orifice throat. In the latter configuration, the second measurement is done at the same ambient temperature conditions, but at different pressure settings.

Another suitable technique to measure the velocity of sound includes the measurement of the travel times of acoustic signals over a path of known length using one or more suitable transmitters and/or receivers. An alternative technique that may be applied to measure the velocity of sound includes the determination of the resonance conditions of a cavity with known characteristics. Such methods are known in the art.

The technique employed to determine the velocity of sound in the fuel preferably has an accuracy of at least ±0.5 m/s, more preferably ±0.1 m/s.

As described below, the method of the present invention may be performed in an iterative manner from an estimated starting point. As a result, the velocity of sound in the fuel gas is required to be calculated. The calculation may be performed using any generally accepted equation of state. Such equations of state are known in the art. Preferably, the velocity of sound in the fuel gas is calculated using the method described in AGA Report No. 10—Speed of Sound in Natural Gas and Other Related Hydrocarbon Gases (American Gas Association 2003).

In a further step, the method requires the concentration of carbon dioxide in the fuel to be determined. Techniques for determining the concentration of carbon dioxide are known in the art. One suitable method employs non-dispersive infrared techniques. The non-dispersive infrared (NDIR) technique consists of measuring the component absorption of infrared light at a specific wavelength in the infrared region. The fundamental vibrational mode (asymmetrical stretching of the molecular bonds) of carbon dioxide is situated in the mid-infrared wavelength spectrum. By selection of the appropriate filter for the incident infrared light, corresponding with this frequency, the concentration of carbon dioxide can be measured in a relatively fast and accurate manner. As an alternative, light absorption techniques could also be applied at other wavelengths such as Near Infrared (NIR, 700-2500 nm) and Far Infrared (FIR, 25-1000 μm), although the light absorption of carbon dioxide is not as pronounced as in the mid infrared area. For carbon dioxide, absorption in the FIR region is due to bending of the bonds of the molecules, while absorption in the NIR domain is due to harmonics of the vibrational energy frequencies. In some cases the absorption may be less influenced by interference of absorption spectra of other molecules in the fuel at these wavelengths, in which case special care must be taken to compensate for the loss in signal strength.

Another technique for measuring the carbon dioxide concentration in fuels includes the use of chemical carbon dioxide gas sensors with sensitive layers based on polymer- or heteropolysiloxane. These techniques have the principal advantage of a very low energy consumption and can be reduced in size to fit into microelectronic-based systems. However, short- and long-term drift effects, as well as a rather low overall lifetime are major obstacles when compared with the NDIR measurement principle.

A further technique for measuring the carbon dioxide concentration in fuels is gas chromatography, where the individual components are separated from each other in a separation column, based on the solubility differences of the components in the stationary phase of the column, and individually measured by a detector at the outlet of the column, such as a Thermal Conductivity Detector or a Flame Ionisation Detector. In addition, mass spectroscopy may also be employed, where the components are ionised and separated from each other in a electro-magnetic field, of which the value is set such that all components are deflected from the detector path with the exception of the component of interest. Again, the use of such techniques and methods to measure the concentration of carbon dioxide in the fuel is known in the art.

The technique employed to measure the molar concentration of carbon dioxide preferably has an accuracy of greater than ±2.0%, more preferably greater than ±1.0% full scale.

The $HV_{m,r}$, the velocity of sound and the molar concentration of carbon dioxide are used to determine the relative density of the fuel. The relative density may be determined as follows:

i. Measure the real molar Heating Value $H_{m,r}$ for the fuel, as described hereinbefore;

ii. Measure the real molar Velocity of Sound $VOS_{m,r}$ of the fuel;

iii. Define a start composition of the fuel which needs to be measured, with the measured concentrations of the first hydrocarbon and carbon dioxide as fixed values;

iv. Calculate the $VOS_{m,r}$ for the start composition;

v. Compare the calculated value of $VOS_{m,r}$ with the value actually measured;

vi. Vary the concentration of each component in the start composition by a small increment to provide a new composition;

vii. Calculate the $VOS_{m,r}$ of the new composition;

viii. Repeat steps 5 to 7 until the difference between the value of $VOS_{m,r}$ as calculated for the composition and as measured is less than 0.002.

ix. Use the final composition to calculate the real molar relative density $RD_{m,r}$.

It has been found that the relative density of the fuel may be determined to an accuracy of within 0.1% using the method of the present invention. Referring to FIG. 7, there is shown a graph of the error in the relative density versus the stoichiometric oxygen (or air)/fuel ratio determined for a wide range of natural gases, with a deviation in the measurement of the velocity of sound of −0.1 m/s and +0.1 m/s. As can be seen, the relative density has been determined to within an accuracy of ±0.1%.

In a further aspect, the present invention provides an apparatus for determining the relative density of a fuel comprising at least one hydrocarbon component, the apparatus comprising:

means for determining the real heating value of the fuel;
means for measuring the velocity of sound within the fuel;

means for measuring the concentration of carbon dioxide in the fuel; and means for determining the relative density of the fuel from the real heating value, the velocity of sound and the concentration of carbon dioxide.

The means for determining the real heating value of the fuel, the means for determining the velocity of sound, and the means for measuring the molar concentration of carbon dioxide may be any suitable means for implementing the techniques discussed hereinbefore.

The means for determining the relative density may be any suitable processor or computer. Suitable processors will be known to the person skilled in the art and are available commercially.

A further aspect of the present invention provides a method for determining the Wobbe Index of a fuel, the fuel comprising at least one hydrocarbon including a first hydrocarbon present in the highest molar concentration, the method comprising determining the heating value of the fuel by:

measuring the stoichiometric oxidation molar flow ratio of the fuel;

determining the ideal molar heating value ($HV_{m,i}$) from the measured stoichiometric oxidation molar flow ratio;

measuring the molar concentration of the first hydrocarbon; and determining the real molar heating value ($HV_{m,r}$) from the ideal molar heating value ($HV_{m,i}$) and the molar concentration of the first hydrocarbon;

determining the relative density of the fuel by:

determining the real heating value of the fuel;

measuring the velocity of sound within the fuel;

measuring the concentration of carbon dioxide in the fuel; and determining the relative density of the fuel from the real heating value ($HV_{m,r}$), the velocity of sound and the concentration of carbon dioxide; and calculating the Wobbe Index from the real heating value ($HV_{m,r}$) and the relative density.

In still a further aspect, the present invention provides an apparatus for determining he Wobbe Index of a fuel, the fuel comprising at least one hydrocarbon including a first hydrocarbon present in the highest molar concentration, the apparatus comprising means for determining the heating value of the fuel comprising:

means for measuring the stoichiometric oxidation molar flow ratio of the fuel;

means for determining the ideal molar heating value ($HV_{m,i}$) from the measured stoichiometric oxidation molar flow ratio;

means for measuring the molar concentration of the first hydrocarbon; and means for determining the real molar heating value ($HV_{m,r}$) from the ideal molar heating value ($HV_{m,i}$) and the molar concentration of the first hydrocarbon;

means for determining the relative density of the fuel comprising:

means for determining the real heating value of the fuel;

means for measuring the velocity of sound within the fuel;

means for measuring the concentration of carbon dioxide in the fuel; and means for determining the relative density of the fuel from the real heating value ($HV_{m,r}$), the velocity of sound and the concentration of carbon dioxide; and means for calculating the Wobbe Index from the real heating value ($HV_{m,r}$) and the relative density.

The present invention also provides various apparatus and specific methods of operation for conducting measurements and determinations of the methods of the preceding aspects of the invention. While a range of equipment designs can be envisaged to practice the steps of the methods of the preceding aspects of this invention, it has been found that the methods are particularly suited to being applied in micro-electro-mechanical systems (MEMS), also sometimes referred to as micro systems technology (MST). The use of MEMS devices is particularly advantageous in the measurement of the stoichiometric oxygen (or air)/fuel molar ratio using the technique of determining the peak combustion temperature. The MEMS technology allows this measurement to be carried out in a flameless mode, which renders the system suitable for use in-line in fuel pipelines and installations. Further, the MEMS device can be operated using very low fuel flow rates, of the order of a few ml or less per minute.

Accordingly, the present invention provides an apparatus for determining the stoichiometric molar ratio of oxygen (or air)/fuel for a hydrocarbon fuel, the apparatus comprising a substrate of inert material having formed therein:

a cavity to serve as an oxidation reactor;

a conduit for the passage of the fuel from an inlet to the cavity; and a conduit for the passage of oxygen (or air) from an inlet to the cavity.

The apparatus is most preferably a MEMS device, as described above, for example an apparatus with the conduits and cavity formed in a chip of inert material. The inert material may be any suitable material as described hereinafter. The conduits and cavity may be formed in the inert material by any suitable techniques, for example by etching. The advantage of the MEMS device is that the apparatus can be very small in size and operate on only a very small volume flowrate of the fuel, resulting in a much higher surface-to-volume ratio and therefore superior control of the internal processes. It has been found that such devices can be used to determine the stoichiometric molar ratio of oxygen (or air)/fuel for the fuels to a very high degree of accuracy. The apparatus may be used in relation to any method requiring the stoichiometric molar ratio of oxygen (or air)/fuel of a fuel to be measured. For example, the apparatus may be used in the calculation of the heating value and/or Wobbe Index of the fuel using any of the methods of the present invention or the prior art, including the method set out in ASTM Standard D-4891, entitled 'Standard Test Method for Heating Value of Gases in Natural Gas Range by Stoichiometric Combustion'.

The apparatus may further comprise a mixer disposed at the inlet to the cavity, such that fuel and oxygen (or air) supplied along their respective conduits are mixed before entering the cavity.

The conduits are formed with inlets or orifices through which fuel or oxygen (or air) may be introduced for passage to the cavity.

The cavity may be empty and the apparatus rely upon mere combustion of the fuel and oxygen (or air). Alternatively, the cavity may comprise one or more catalyst compositions that are active in promoting the oxidation of hydrocarbons to improve the reaction kinetics by lowering the activation energy and favouring specific reaction products. Examples of suitable catalysts include noble metals, such as platinum, iridium, palladium or rhodium.

The substrate of inert material is preferably formed using production techniques employed in the manufacture of semiconductors, that is the components are formed by removing material from the substrate and/or the deposition of material onto the substrate. The inert material may be any of the materials known for use in MEMS devices, in particular polymers, metals, silicon or glass. Suitable polymer materials are known and commercially available and must be capable of resisting the conditions generated by the flameless oxidation of the fuel. The polymer material may be formed with the components of the apparatus by techniques known in the art, in particular injection moulding, embossing and stereolithography. Metals may be employed as the inert material, in particular gold, nickel, aluminium, chromium, titanium, platinum, tungsten, silver, palladium, iridium and rhodium. Metals may be formed using such techniques as electroplating, evaporation and sputtering processes. The preferred materials for use as substrate materials in the apparatus of the present invention are silicon and glass, formed using a combination of deposition, lithographic and etching techniques.

It is an advantage that the cavity formed in the substrate to serve as an oxidation reactor can be of very low volume, resulting in a compact device that require a very low volume of both fuel and oxygen (or air) to operate and that has a very fast response time. The cavity may have a volume of less than 1 ml, more preferably less than 500 µl, with cavities having a volume of about 1 µl or less being especially preferred. The conduits for providing passage of the fluids to the cavity will have dimensions, in particular internal diameters, corresponding to the volume of the cavity, such that the residence time of the measured gases in the cavity is long relative to the residence time in the supply and outlet conduits.

The substrate is preferably formed as a chip of the inert material, in particular a chip of silicon and/or glass.

The apparatus preferably further comprises a temperature sensor formed within or on the substrate to monitor the temperature of oxidation reactions taking place in the cavity.

The conduits formed to provide passage for the fuel and oxygen (or air) being supplied to the cavity are sized to provide the required flow rates of the fuel and oxygen (or air) to be reacted. It is a particular advantage of the MEMS devices that the conduits and their respective orifices may be accurately formed to provide the required fluid flow, thus obviating the need for any moving parts in the device to control the fluid flow rate. Alternatively, the apparatus may be provided with means for controlling the flow of fluids through the conduits to the cavity.

The apparatus preferably further comprises one or more heaters to pre-heat the fuel and/or oxygen (or air) flowing along the respective conduit, prior to entering the cavity and taking part in the oxidation reaction, and/or to control the temperature of the apparatus. The preferred materials for use in the apparatus as heaters and sensors are noble metals, such as gold, platinum, rhodium, iridium and palladium.

In one preferred embodiment, the apparatus is formed from a block, in particular a chip, of inert material comprising a base and a cover, each of the cavity and the conduits for oxygen (or air) and fuel, and the temperature sensor and heater(s), if present, being formed in one of the cover and the base. In one preferred arrangement, the cavity and the conduits, with integrated orifices and mixer for both oxygen (or air) and fuel, are formed in one of the cover and the base, preferably the base, with the other of the cover and the base having formed therein both the temperature sensor and one or more heaters.

A single apparatus may be provided with means for varying the flow rate of fluids through the conduits, as mentioned above, and used to measure the temperature of oxidation of a fuel at a range of oxygen (or air) to fuel ratios. This may be achieved by varying the flow rate of the fuel and/or the oxygen (or air) to the cavity. However, as noted above, it is a particular advantage of the present invention and its use of MEMS technology that the flow rate of fluid through the conduits may be determined by the dimensions of the conduit, in particular the cross-section of the orifices of the conduit. Thus, a given apparatus may be formed to provide a predetermined flow rate of oxygen (or air) and a predetermined flow rate of fuel to the cavity, thus allowing the apparatus to operate at a fixed oxygen (or air)/fuel ratio.

As discussed hereinbefore, the stoichiometric molar flow ratio of oxygen (or air) and fuel for a given fuel is determined by measuring the peak oxidation temperature or the oxygen (or air) concentration at the outlet of the combustion chamber. This is achieved by measuring the oxidation temperature or the oxygen (or air) concentration at the outlet of the combustion chamber for a range of oxygen (or air)/fuel ratios.

In one embodiment, this is achieved using the apparatus described hereinbefore, having a single reactor assembly, and providing the apparatus with a means for varying the flow of one or both of the fuel and oxygen (or air) being supplied through their respective conduits to the mixer and then the cavity. The means for varying the flow rate of one or both the fuel and oxygen (or air) is preferably incorporated into the substrate.

One means to vary the flow rate of the fuel and/or the oxygen (or air) through the conduit to the cavity is by measuring and regulating the fluid pressure upstream of an orifice, such that critical flow is generated in the orifice, which is independent of small downstream pressure variations. The actual flow rate can than be calculated from the measurement of the upstream pressure, and the orifice geometry. An alternative means to vary the flow rate of the two fluids is by measuring and regulating the fluid pressure upstream and downstream of an orifice. The actual flowrate can than be calculated from the measurement of the upstream and downstream pressure, and the orifice geometry. The pressure regulation of the gases for the aforementioned techniques can be achieved with mechanical and/or electronic pressure regulators.

An alternative means to vary the flow rate of the two fluids is to employ a parallel configuration of different flow paths, with each operating under the same pressure conditions, but with each having incorporated therein a different orifice section, such that with the parallel configuration the complete range of required flow rates for the gases can be provided, given a defined set of upstream and downstream pressures.

A further alternative means of varying the flow rate through the combustion cavity is by filling a fixed volume chamber with the fluid up to a predefined pressure. The inlet to the fixed volume chamber is closed, and an outlet, which leads the fluid through an orifice to the combustion cavity, is opened. By continuously monitoring both the pressure in the fixed volume chamber and the temperature of the oxidation reaction, the molar flow rate at the stoichiometric combustion point can be defined.

Still a further alternative means to vary the flowrate of the two fluids is through the use of mass flow controllers for each supply gas, based on thermal flow measurement. Such controllers comprise a thermal sensor, which is essentially a small bore tube with two resistance-thermometer elements wound around the outside of the tube. The sensor tube is heated by applying an electric current to the elements. A constant proportion of the gas flows through the sensor tube, and the cooling effect creates a temperature differential between the two elements. The change in the resistance due to the temperature differential is measured as an electric signal. This is used as control signal to operate a proportional control valve, in turn to control the flow rate of gas through the valve and into the conduit.

In operation, both fuel and oxygen (or air) are fed to the mixer of the oxidation cavity, where the fuel is oxidised and the temperature of oxidation or the outlet oxygen (or air) concentration is recorded. The molar flow rate of one of the fuel and oxygen (or air) is kept constant. The molar flow rate of the other of the fuel and oxygen (or air) is changed, either being increased or decreased, stepwise or continuously, to vary the molar ratio of oxygen (or air) and fuel being supplied to the cavity. In this way, the temperatures of oxidation or the outlet oxygen (or air) concentration over a range of different oxygen (or air)/fuel molar ratios may be measured and the peak temperature or oxygen (or air) depletion point, corresponding to the stoichiometric oxidation ratio, identified. The cycle of varying the flow rate of one component may be repeated.

Accordingly, in a further aspect the present invention provides a method of determining the stoichiometric oxidation ratio for a fuel, the method comprising the steps of:

providing a reactor for conducting the oxidation of the fuel with oxygen (or air);

supplying oxygen (or air) to the reactor;

supplying the fuel to the reactor;

maintaining the flow rate of one of the fuel and oxygen (or air) to the reactor constant;

varying the flow rate of the other of the fuel and oxygen (or air) to the reactor, in order to vary the molar ratio of the fuel and oxygen (or air) being reacted;

measuring the temperature of the oxidation reaction or the oxygen (or air) concentration at the outlet of the combustion cavity over a range of molar ratios; and determining the stoichiometric oxidation ratio from the peak temperature or the oxygen (or air) concentration at the outlet of the combustion cavity.

As noted above, the method preferably employs a mixer upstream of the reactor, such that the incoming fuel and oxygen (or air) are well mixed prior to combustion or oxidation in the reactor.

In an alternative arrangement, the required range of molar flow ratios may be analysed using a plurality of separate reactor assemblies, one for each molar flow ratio. The apparatus of the present invention may be arranged with a plurality of reactor assemblies in parallel to allow a series of oxidation reactions using a single source of fuel and oxygen (or air) to be monitored and the peak oxidation temperature identified. This is achieved by arranging in parallel a plurality of devices having conduits with different orifice sections allowing different molar flow rates of fuel and oxygen (or air) each from a single source. In one arrangement, a plurality of separate devices is arranged with the reactor assemblies in parallel. In an alternative arrangement, a single device is provided with a plurality of cavities, each oxidation cavity having its own respective conduits with specific orifice sizes, for providing a flow of oxygen (or air) and fuel to the cavity, the conduits for each cavity being arranged to provide fuel and oxygen (or air) to the cavity at a specific predetermined molar ratio by means of specific orifice sizes.

Again, a mixer is preferably employed upstream of each cavity.

The different molar flow rates of fluid through the conduits may be achieved in several ways. For example, the conduits for the passage of oxygen (or air) may all be formed with orifices of the same cross-sectional-area, while the conduits for the passage of the fuel have orifices of differing cross-section area. Alternatively, the conduits for the passage of the fuel may be identical, with the variation in molar ratio being achieved by differing sizes of openings in the oxygen (or air) conduits. A further more complicated alternative is to employ different orifice sections in both the oxygen (or air) and fuel conduits, as required. The choice of approach in this respect may depend upon such factors as the range of orifice sections that may be achieved by the technique being used to prepare the device.

Accordingly, in a further aspect, the present invention provides an apparatus for determining the stoichiometric molar flow ratio for oxidation of a fuel, comprising a substrate of inert material the substrate having formed therein:

a first inlet for the fuel;

a second inlet for oxygen (or air);

an outlet for reacted fluid; and a plurality of reactor assemblies, each reaction assembly comprising:

a cavity;

a first conduit extending between the cavity and the first inlet for passage of the fuel to the cavity;

a second conduit extending between the cavity and the second inlet for passage of oxygen (or air) to the cavity;

an outlet conduit extending between the cavity and the outlet; and a temperature sensor for measuring the temperature of fluids reacting within the oxidation cavity, or a sensor to measure the oxygen (or air) concentration at the outlet of the oxidation cavity;

wherein each reactor assembly is arranged to provide the fuel and oxygen (or air) to the cavity in a different predetermined molar ratio.

As noted above, a mixer is preferably provided to ensure proper mixing of the fuel and oxygen (or air) prior to entering the cavity.

The apparatus having the reactor assemblies arranged in parallel allows for the simultaneous measurement of oxidation temperatures at a range of oxygen (or air)/fuel molar ratios. This provides the apparatus with a very fast response time and a high degree of accuracy and repeatability.

The apparatus may further comprise one or more heaters for each reactor assembly, to preheat either one or both of the fuel or the oxygen (or air) before entry into the cavity, and/or to control the temperature in the cavity before and during the oxidation reaction.

The apparatus is most advantageously arranged with all the reactor assemblies in a single block or chip. The apparatus most preferably employs MEMS technology, the details of the arrangement being as hereinbefore described. In this way, a single device may be provided that can receive a single supply of each of the fuels to be analysed and oxygen (or air) and produce a range of temperature readings for oxidation of the fuel at a range of different oxygen (or air)/fuel ratios. The outputs of the temperature sensors are each correlated to a specific flow ratio, according to the relative dimensions of the orifices of the respective reactor assembly. A suitable processor can extrapolate and interpolate the output temperatures, in order to identify the peak oxidation temperature and the stoichiometric oxygen (or air)/fuel ratio.

The present invention provides a corresponding method for determining the stoichiometric molar flow ratio for oxidation of a fuel, the method comprising:

providing a plurality of reactor assemblies, each reaction assembly comprising:

a oxidation cavity;

a first conduit for passage of the fuel to the cavity; and a second conduit for passage of oxygen (or air) to the cavity;

wherein each reactor assembly is arranged to provide the fuel and oxygen (or air) to the cavity in a different predetermined molar ratio;

supplying fuel to the first conduit of each reactor assembly;

supplying oxygen (or air) to the second conduit of each reactor assembly;

controlling the molar flowrate of fluid in each conduit with an internal orifice;

allowing oxidation of the fuel to occur in each cavity;

measuring the temperature of oxidation in each cavity, or the oxygen (or air) concentration at the outlet of the cavity; and determining the stoichiometric oxidation molar ratio from the measured temperatures and the predetermined molar flow ratios.

As noted above, the stoichiometric oxidation molar flow ratio is determined by interpolating the oxidation temperature/molar flow ratio relationship across the plurality of reactor assemblies. The method is most advantageously conducted with all the reactor assemblies operating simultaneously in parallel with fuel and oxygen (or air) being supplied from a single source.

As will be appreciated, the accuracy of the determination will be improved with a greater number of parallel reactor assemblies. The apparatus and method preferably employ at least 4 parallel reactor assemblies, more preferably at least 8 assemblies. Arrangements employing at least 10, more preferably at least 20 parallel reactor assemblies are particularly advantageous, in particular for heavier fuels, such as LPG. An advantage of the MEMS technology is that a large number of parallel reactor assemblies may be formed in a single chip or device.

As noted hereinbefore, the cavity may be empty, or may be provided with one or more catalysts. The specific type and placement of the catalyst may depend on the type of fuel to be analysed. Possible catalysts for the oxidation of hydrocarbon fuels include platinum, iridium, palladium and rhodium.

In order to readily identify the peak oxidation temperature, the apparatus should be adapted and the methods operated over a range of molar flow ratios of oxygen (or air) to fuel which encompass the stoichiometric oxidation molar flow ratio for the range of fuels to be analysed. Thus, for natural gas and liquefied natural gas (LNG), this ratio may be from 1.0 to 3.0, more preferably from 1.3 to 2.6, while for higher fuels the range of molar ratios will be greater. For example for LPG analysis, the molar flow ratio will be from 2.5 to 5.5, more preferably from 3.0 to 5.0.

As discussed in detail hereinbefore, the ideal molar heating value $HV_{m,i}$ is determined from the stoichiometric oxidation molar flow ratio of the fuel, which is then corrected using a measurement of the concentration of the first hydrocarbon, to provide the real molar heating value $HV_{m,r}$. Accordingly, the aforementioned apparatus of the present invention may further comprise means for measuring the concentration of the first hydrocarbon. Such means may employ any suitable measurement technique, as described above, for example infrared analysis of the fuel being fed to the inlet of the apparatus.

As also discussed in detail above, a determination of the relative density of the fuel is required if the Wobbe Index is to be calculated. As discussed, the relative density is preferably determined using a measurement of the velocity of sound in the fuel and the concentration of carbon dioxide in the fuel. Advantageously, the aforementioned apparatus further comprise means for measuring the velocity of sound in the fuel and the concentration of carbon dioxide in the fuel.

The velocity of sound in the fuel may be measured by passing the fuel at a specific flow rate through an orifice of a known diameter and the velocity of sound measured using an appropriate sensor. It is an advantage of the MEMS technology that a conduit having a suitable orifice or throat may be formed in the substrate using the aforementioned techniques. Preferably, the conduit is formed in the same substrate block or chip as the reactor assemblies and other components. In this way, the same fuel supply and inlet may be used for the determination of the oxidation temperature and the velocity of sound.

Typically, the orifice or throat of the conduit will have a cross-sectional area less than 1000 $\mu m^2$. A thin film sensor may be etched at the location in the conduit where the velocity of the fuel reaches that of sound. It is preferred that the velocity of the fuel passing through the conduit is measured at another location in the conduit, in order to allow the measurement of the velocity of sound to be corrected for influences of density, viscosity and heat capacity.

BRIEF DESCRIPTION OF THE DRAWINGS

Embodiments of the present invention will now be described, by way of example only, having reference to the accompanying figures, in which:

FIG. 8A is a perspective view of an apparatus according to one embodiment of the present invention for the determination of the peak oxidation temperature of a fuel;

FIG. 8B is an example of the base of the apparatus of FIG. 8A;

FIG. 8C is an example of the cover of the apparatus of FIG. 8A;

FIG. 8D shows a processor for calculating the real molar heating value;

DETAILED DESCRIPTION OF THE INVENTION

Figure 1:
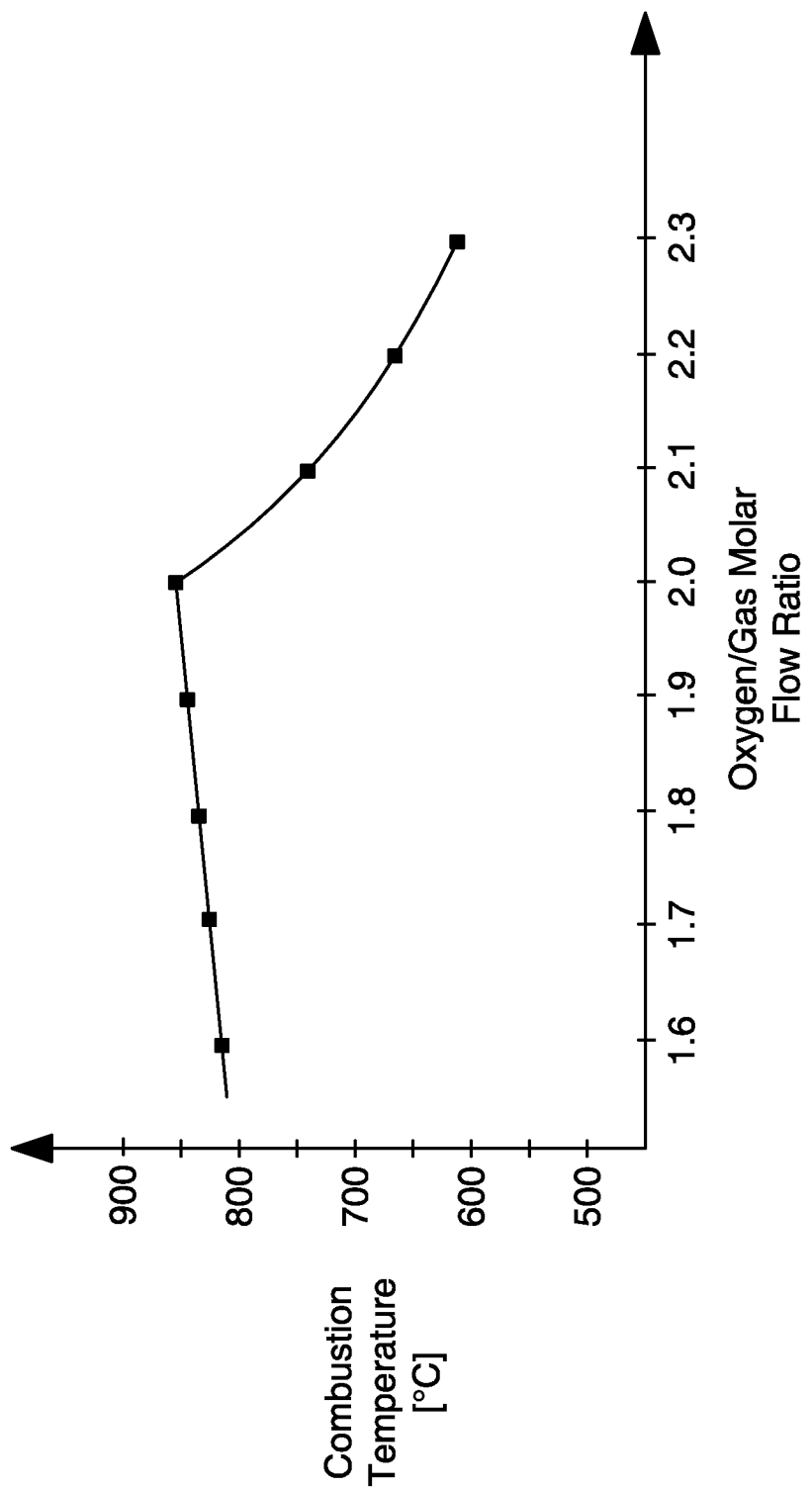
FIG. 1 is a graph of the temperature of combustion of a gaseous fuel in oxygen (or air) against the variations in the oxygen (or air)/gas molar ratio.
Figure 2A:
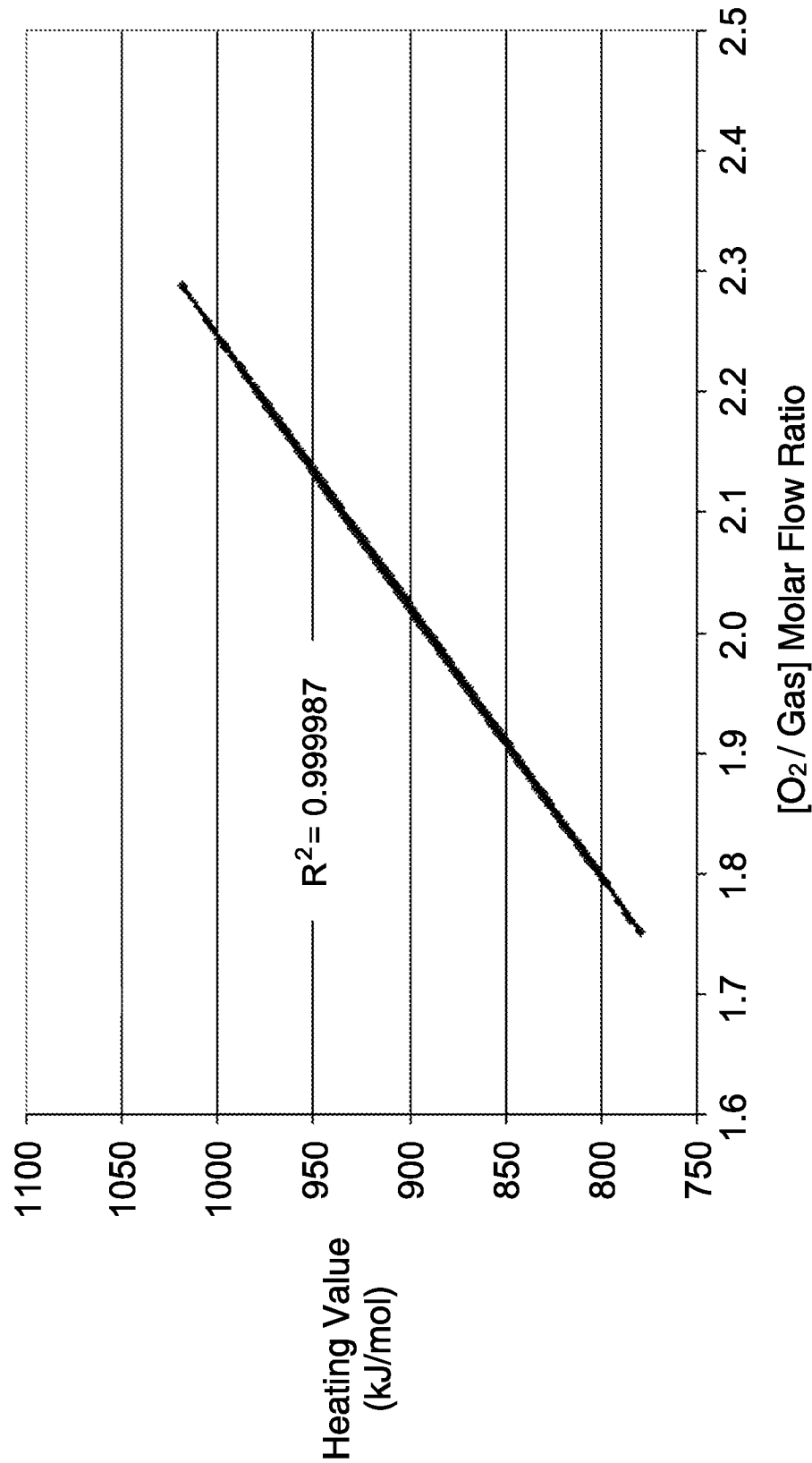
FIG. 2A is a graph of the ideal molar heating value $HV_{m,i}$ of a range of 1000 random natural gas compositions against the stoichiometric oxidation ratio of the fuel.
Figure 2B:
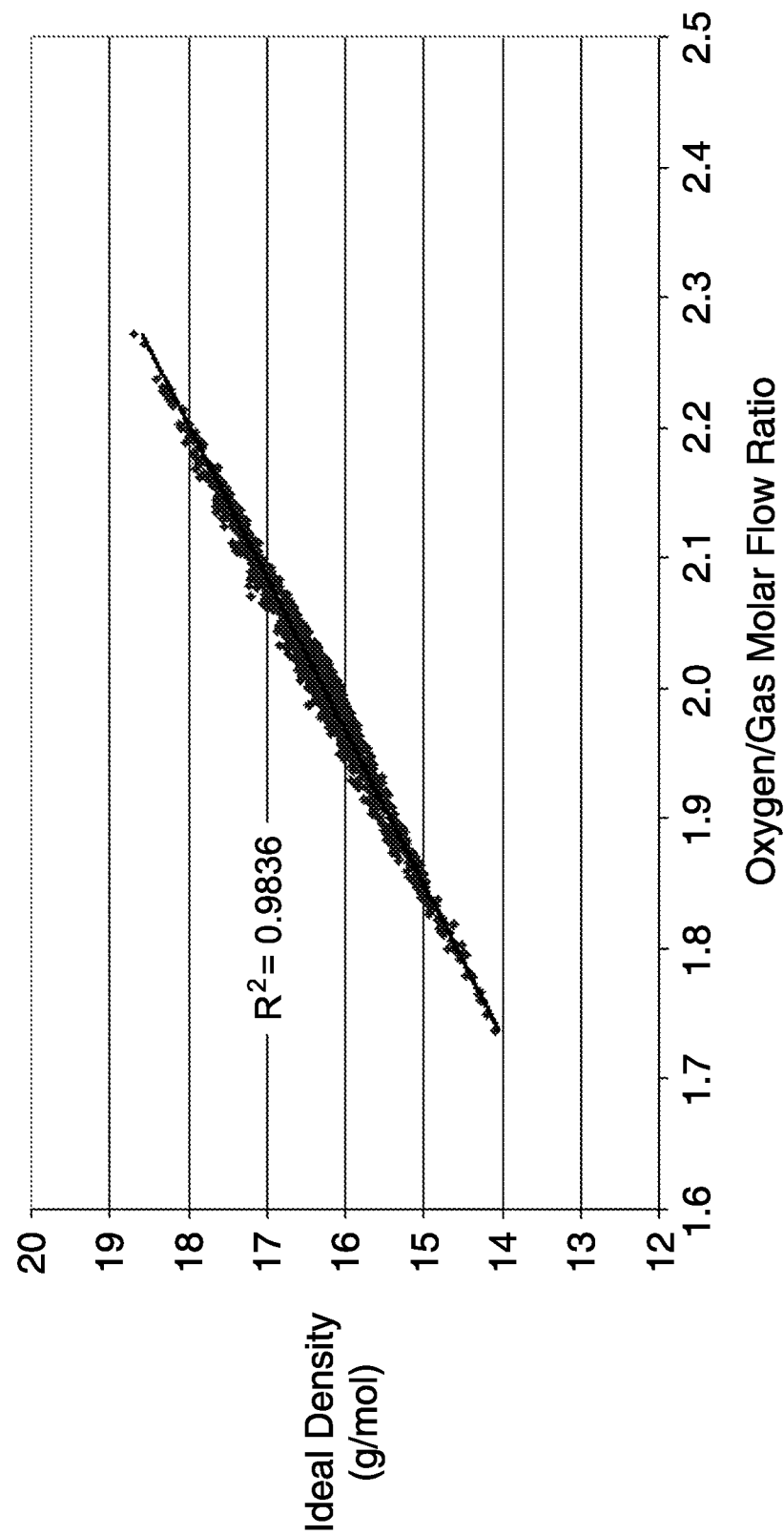
FIG. 2B is a graph of the ideal molar relative density $RD_{m,i}$ of a range of 1000 random natural gas compositions against the stoichiometric oxidation ratio of the fuel.
Figure 3:
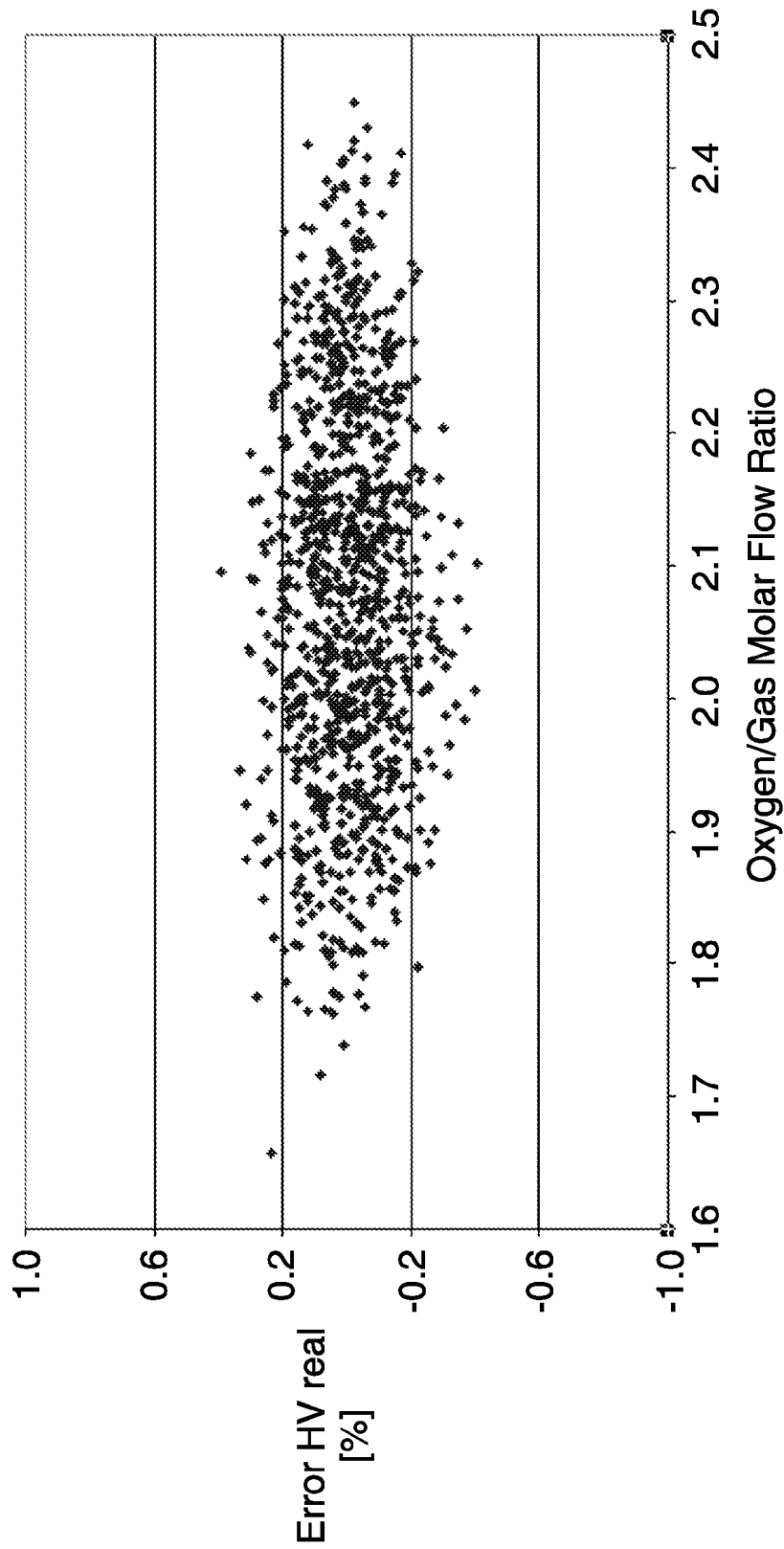
FIG. 3 is a graph of the error in the real molar heating value $HV_{m,r}$ for the range of random natural gas compositions of FIG. 2a against the stoichiometric oxidation ratio of the fuel.
Figure 4:
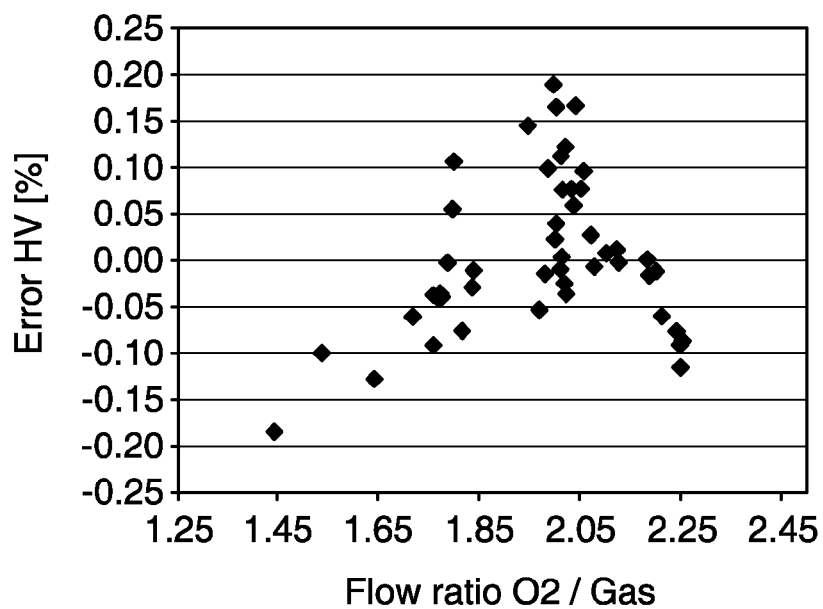
FIG. 4 is a graph of the error in the real molar heating value $HV_{m,r}$ for a range of natural gases commercially supplied worldwide against the stoichiometric oxidation ratio of the fuel.
Figure 5:
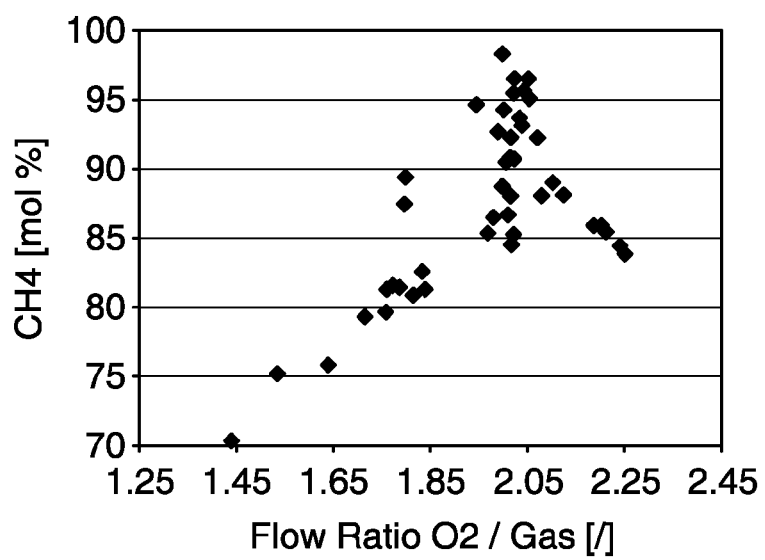
FIG. 5 is a graph of the molar methane concentration against the stoichiometric oxidation ratio of the fuels of FIG. 4.
Figure 6:
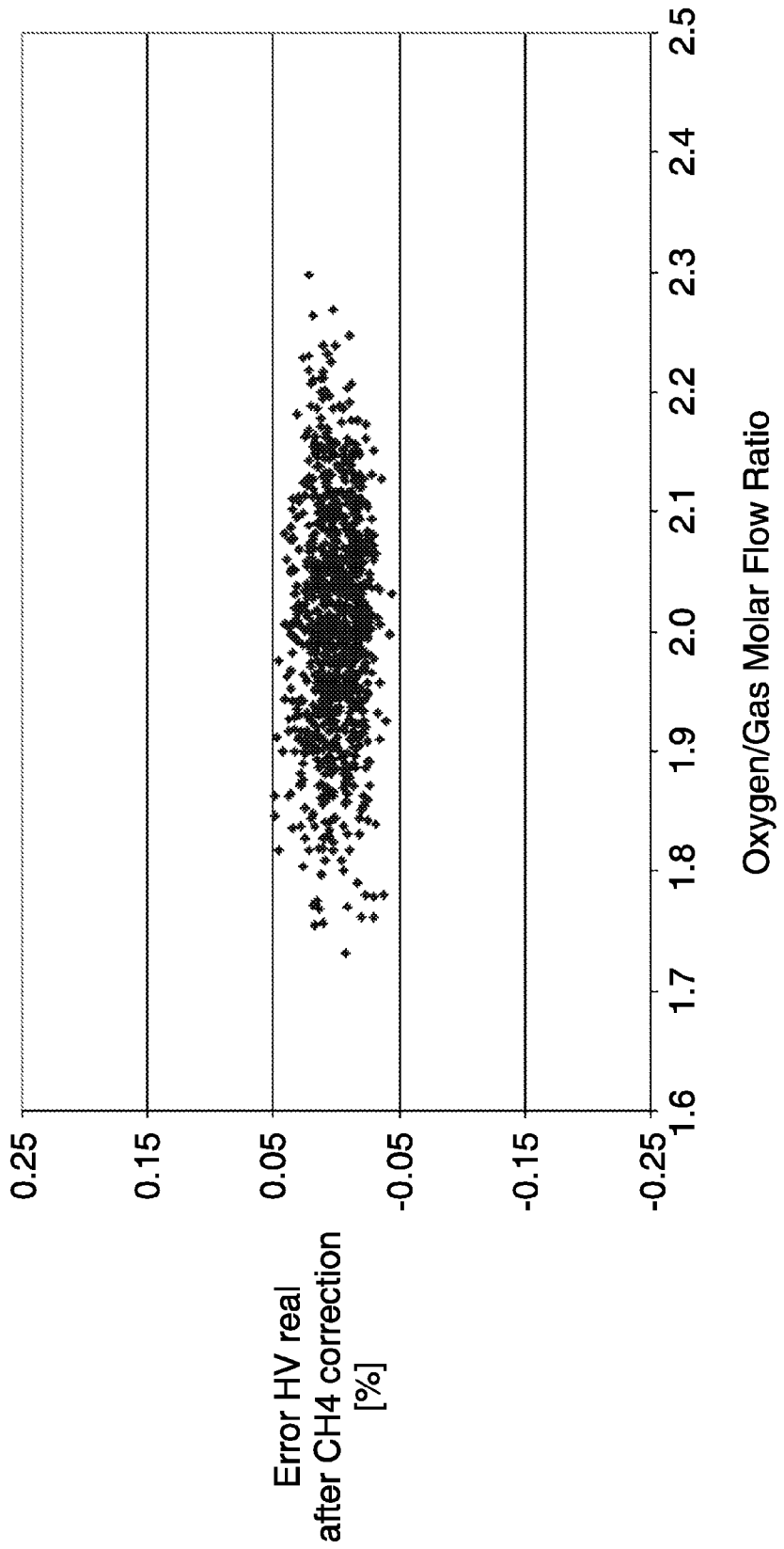
FIG. 6 is a graph of the error in the real molar heating value $HV_{m,r}$ against the stoichiometric oxidation ratio of the range of fuel compositions of FIG. 2a after correction from the measurement of the first hydrocarbon (which is methane for the displayed range)
Figure 7:
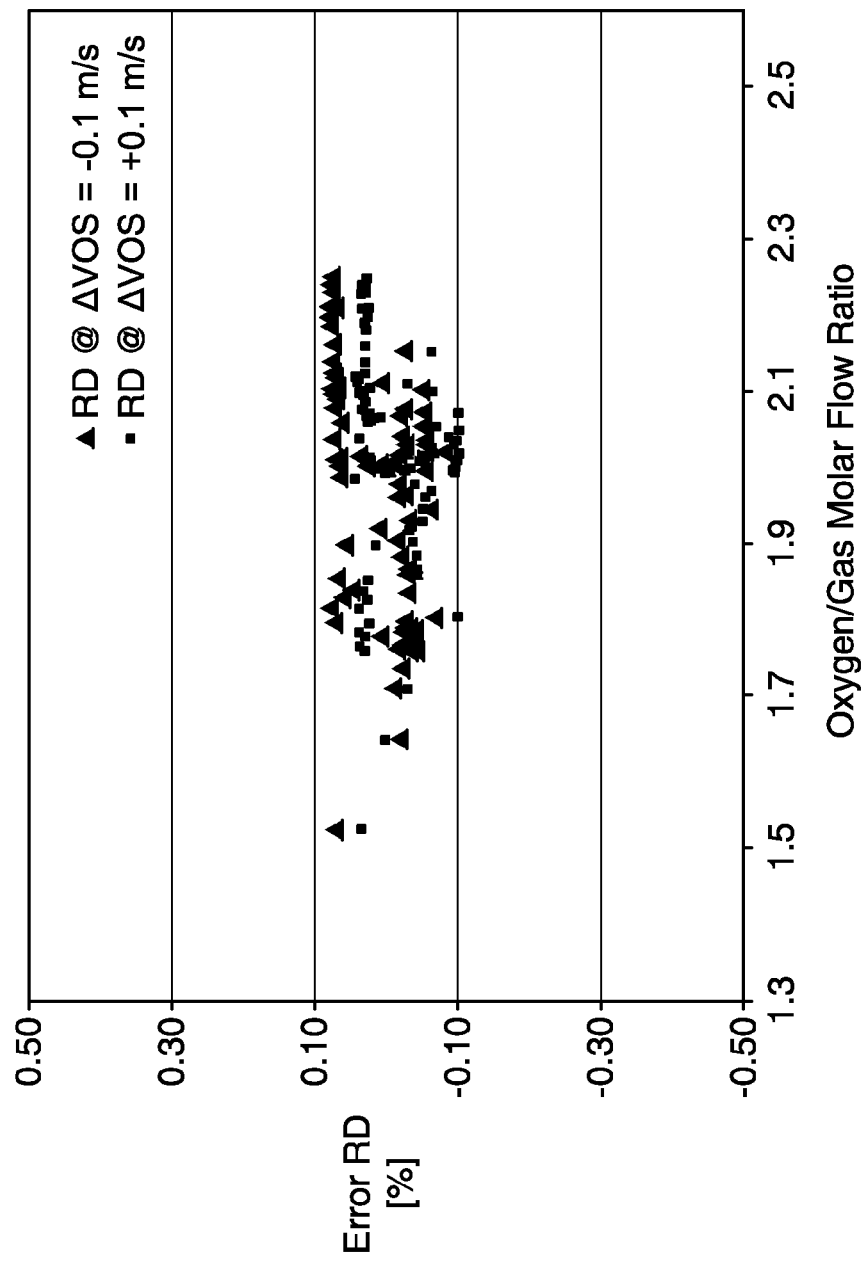
FIG. 7 is a graph of the error in the determination of the relative density of the range of gas compositions of FIG. 2b based on the measurement of the velocity of sound against the stoichiometric oxidation ratio of the fuel after correction from the measurement of the first hydrocarbon and the carbon dioxide concentration.

Referring to FIG. 8A, there is shown an example of an apparatus, generally indicated as 2, for measuring the oxidation temperature of a fuel/oxygen (or air) mixture. The apparatus 2 is in the form of a chip of silicon or glass and comprises a base 4 and a cover 6, details of which are shown in FIGS. 8B and 8C respectively.

The base 4, shown in plan view with the cover 6 removed in FIG. 8B, has a total of eight reactor assemblies 8 etched into one major surface. Each reactor assembly 8 comprises a cavity 10 in which the fuel and oxygen (or air) are caused to react in a flameless oxidation reaction. The cavity 10 has extending therefrom an inlet conduit 12 for an oxygen (or air)/fuel mixture and an outlet 14 for the combustion products. The inlet conduit 12 has at its distal end a gas mixer 16 into which an oxygen (or air) conduit 18 and a fuel conduit 20 open. Each of the oxygen (or air) and fuel conduits 18, 20 is provided with an orifice or throat, 22 and 24 respectively, the size of which is selected to determine the molar flow rate of gas flowing in the respective conduit. The base 6 is further provided with a fuel inlet header conduit 26 connected to each fuel conduit 20 and having an inlet 28 for receiving fuel from a supply (not shown for clarity). A similar header conduit (not shown for clarity) is provided for the supply of oxygen (or air) to each oxygen (or Nr) conduit 18. An outlet header 30 is connected to each outlet conduit 14 and has an outlet 32 for the removal of the products of combustion. The molar concentration of the first hydrocarbon is measured by standard technology, such as non-dispersive infrared, gas chromatography or mass spectroscopy, upfront in a gas channel 40.

Each cavity 10 is provided with an ignition circuit (not shown) etched into the base 6 for initiating the flameless oxidation reaction.

Referring to FIG. 8C, the cover 6 comprises an array of heater elements 34 for controlling the temperature of the oxygen (or air) and fuel in their respective conduits and being supplied to the cavities 10. The cover 6 further comprises a temperature sensor element 36 for each cavity 10, for measuring the temperature of gases within the cavity. The temperature sensor elements 36 are all linked to a central processor (not shown for clarity), for receiving and processing the outputs of the sensors.

The cavities 10 and the conduits of the reactor assemblies 8 are sealed by a thin membrane seal.

The chip is a compact, multi-reactor apparatus, having dimensions which are typically in the order of 10 mm in width and 10 mm in length.

In operation, fuel to be analysed is supplied to the inlet 28, where it enters the fuel inlet header conduit 26 and flows into each of the fuel conduits 20. The molar flow rate of the fuel through the conduit and to the cavity is determined by the dimensions of the throat 24 in the fuel conduit 20. Similarly, oxygen (or air) is supplied to each oxygen (or air) conduit 18, the molar flow rate of which in each conduit is determined by the dimensions of the throat 22. Each reactor assembly 8 operates a different, known molar ratio of fuel and oxygen (or air).

The oxygen (or air) and fuel are thoroughly mixed in the mixer 16, before passing along the inlet conduit 12 to the respective cavity 10, where they are caused to react. The temperature of the oxidation reaction in each cavity 10 is measured by the sensor 36. The products of the oxidation leave the cavity along the outlet conduit 14 and exit the apparatus via the outlet header 30 and the outlet 32.

In this way, a total of 8 oxidation reactions at 8 different molar ratios of oxygen (or air) and fuel are performed simultaneously, the temperatures of which are measured and sent to the central processor. The peak oxidation temperature is determined by interpolating the measured temperature values and the corresponding stoichiometric oxidation flow ratio determined.

The real molar heating value ($HV_{m,r}$) is calculated from the ideal molar heating value ($HV_{m,i}$) and the molar concentration of the first hydrocarbon. This is further illustrated in FIG. 8D, where a processor 42 is shown to calculate the real molar heating value ($HV_{m,r}$).

Figure 9A:
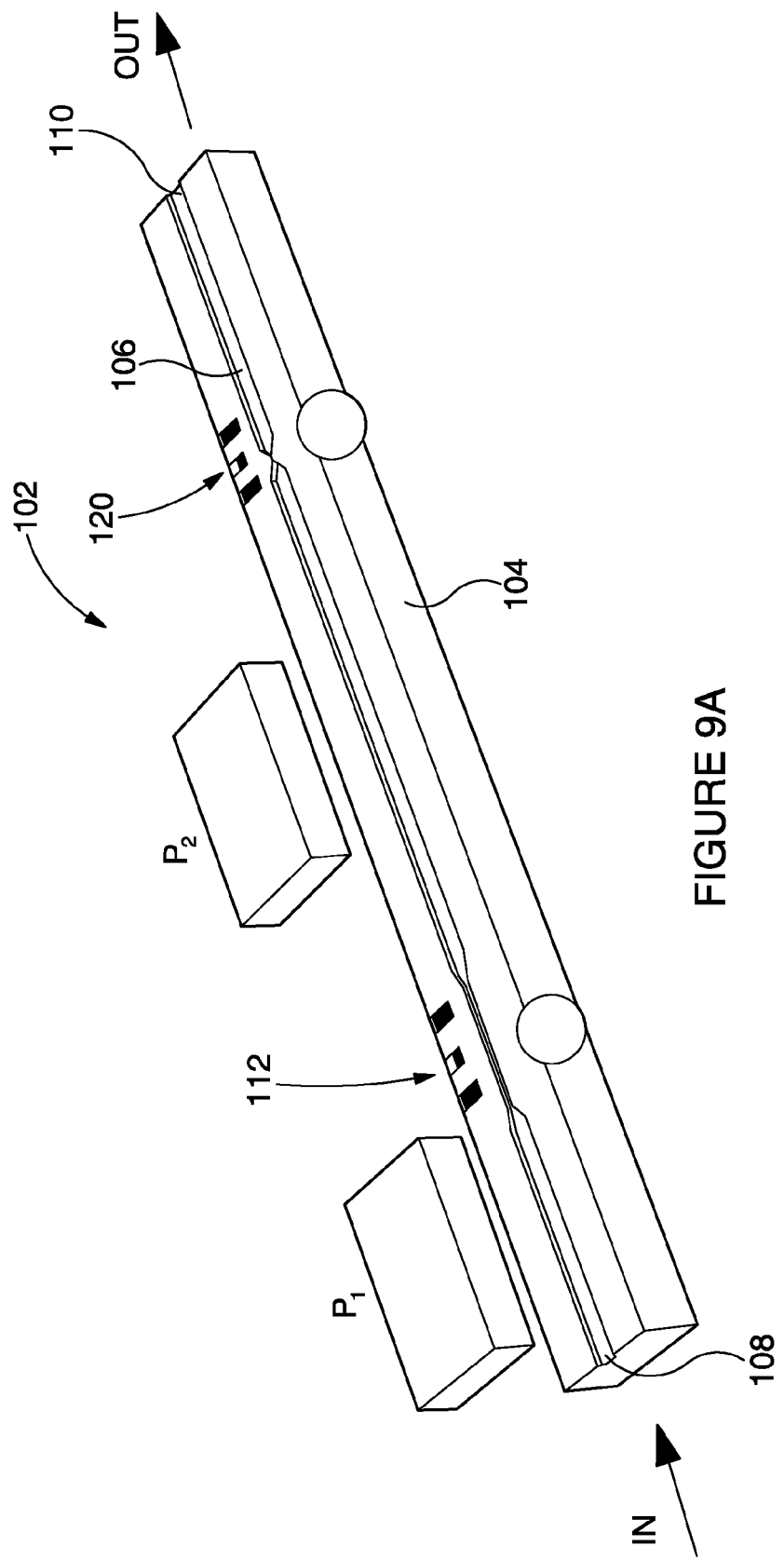
FIG. 9A is an embodiment of a sensor for measuring the velocity of sound in a hydrocarbon fuel.

Turning to FIG. 9A, there is shown a sensor for use in determining the velocity of sound in a gas, in particular a gaseous hydrocarbon fuel. The sensor, generally indicated as 102 comprises a base 104 formed from a chip of inert material. The sensor is 10 mm long and 1 mm in width. A channel 106 is etched into the surface of the base 104. The channel 106 has an inlet end 108 and an outlet end 110.

Figure 9B:
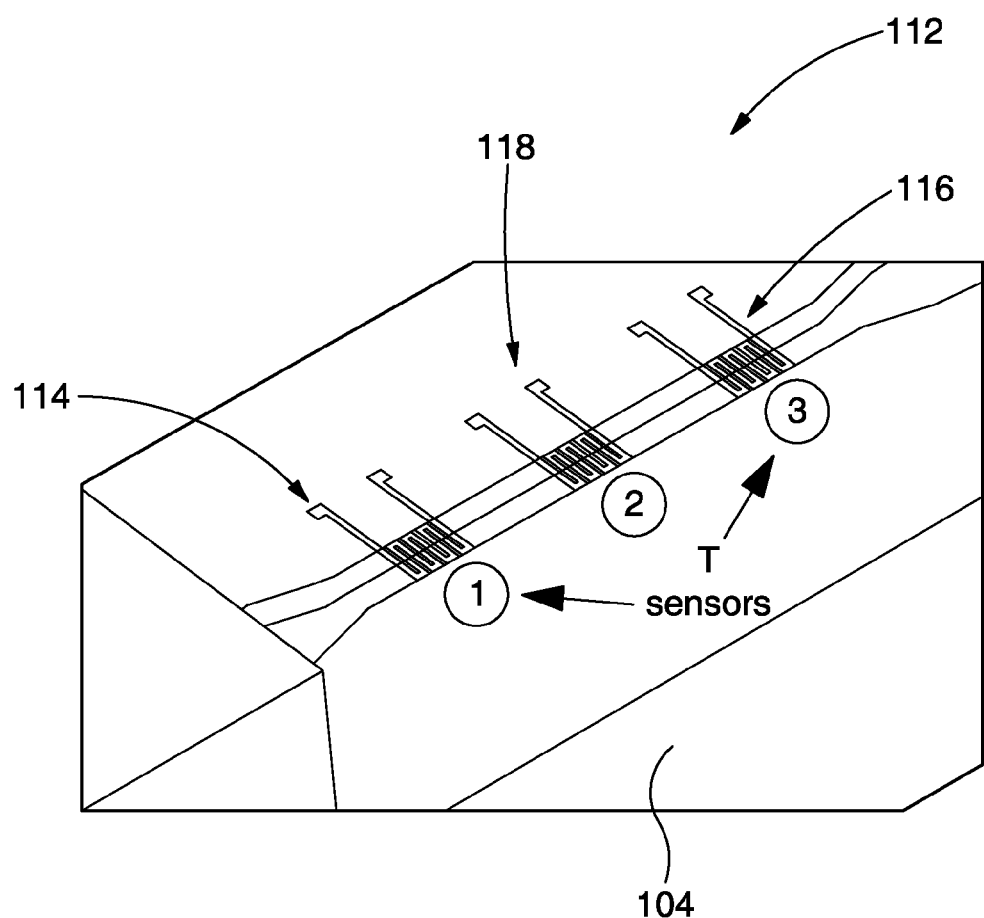
FIG. 9B is a enlarged view of a portion of the sensor of FIG. 9A.

The channel has a constriction 112, that is a portion of its length of reduced cross-sectional area, in the region of the inlet 108, shown in more detail in FIG. 9B. The sensor is provided with temperature sensors 114 and 116, in the form of thin film tracks of noble metal, in particular silver, gold, platinum, rhodium, iridium or palladium, terminating in square contact pads. A heater element 118 of the same general configuration and construction as the temperature sensors 114 and 116 is disposed between the temperature sensors.

An orifice 120 is disposed in the region of the outlet 110, having three sensors in the same arrangement and type as the constriction.

A cover (not shown for clarity) is provided to extend over the base. The cover serves to seal the channel 106. In addition, the cover has contacts to provide connections to the heaters and sensors from external control and measurement devices.

EXAMPLE

The determination of $HV_{real}$ and $RD_{real}$ of a fuel gas was carried out using the method of the present invention as follows.

To demonstrate the methods of the present invention, the following gas composition (amounts of each component specified as % mol) was compiled:

| | |
|---|---|
| He | 0.0230 |
| $N_2$ | 6.4885 |
| $CH_4$ | 80.0639 |
| $CO_2$ | 0.4970 |
| $C_2H_6$ | 10.9504 |
| $C_3H_8$ | 0.5030 |
| $C_4$ | 0.7029 |
| $C_5$ | 0.5632 |
| $C_6+$ | 0.2081. |

The composition was determined to have an oxygen/gas molar ratio of 2.120 and a velocity of sound ($VOS_{m,r}$) of 435.0 m/s. Errors were introduced into the data to simulate the inaccuracies that are typically encountered in the field. In particular, the VOS was provided with an uncertainty of 0.1 m/s. The concentrations of both $CH_4$ and $CO_2$ were provided with errors of 1%. Finally, the oxygen/gas stoichiometric ratio was provided with an error of 0.01%, equivalent to an uncertainty of 0.1° C.

It will be noted that the composition does not follow the ⅓ rule, having a ratio of ethane to propane of about 20 and equal concentrations of $C_4$, $C_5$ and $C_6$. Accordingly, such instruments as a Correlative Meter could not be used to analyse the gas composition.

The composition was calculated to have a $HV_r$ of 42.245 MJ/m³, a RD, of 0.6712 and a compressibility factor Z of 0.9969.

The following algorithm was used to determine a start composition:

$$(i=2\ldots N): C_{i,0}=LIMIT_i/\Sigma_i(LIMIT_i)*(100-C_{1,0})$$

where $C_j$ is the concentration of component i in the composition above; $C_1$ is the concentration of the first hydrocarbon (measured value, fixed); N is the number of significant components expected in the fuel (9 in the case of natural gas); and $LIMIT_i$ is the maximum concentration of component i for which the method is applicable, as given below:

| | |
|---|---|
| He | 0.05 |
| N₂ | 20.00 |
| CH₄ | 60.00 |
| CO₂ | 15.00 |
| C₂H₆ | 15.00 |
| C₃H₈ | 6.00 |
| C₄ | 1.50 |
| C₅ | 1.00 |
| C₆+ | 0.20 |

A start composition for the determination of $HV_{real}$ and $RD_{real}$ of the gas composition (% mol) was defined as follows:

| | |
|---|---|
| CH₄ | 80.46 |
| N₂ | 8.70 |
| CO₂ | 0.50 |
| C₂H₆ | 6.53 |
| C₃H₈ | 2.61 |
| iC₄ | 0.33 |
| nC₄ | 0.33 |
| iC₅ | 0.22 |
| nC₅ | 0.22 |
| C₆+ | 0.09 |
| He | 0.02 |

Determination of Real Molar Heating Value ($HV_{m,r}$)

Starting from the initial gas fuel composition, iteration using the above algorithm was conducted to gradually change the composition of each of the different components such that $HV_{m,i}$ (the molar ideal HV) calculated from this composition, converges with $HV_{m,i}$ calculated from the correlation curve ($HV_{corr}=455.152*\phi+0.0654$). The iteration is guided by certain limits for $\Delta HV_{m,i}$ and $\Delta D_{m,j}$, as follows:

1. Starting from the initial composition $\psi 0$, $2^{(N-2)}$ compositions are proposed per iteration step, with N the number of components in the gas, (which is 9 for natural gas). Each composition differs from each other by the concentration of only one component, which is equal to $\pm(\Delta*C_{i,j})$, with $\Delta$ a certain step value, and $C_{i,j}$ the concentration of component i of the hypothetical composition j.

2. For each composition, $\Delta HV_{m,i}$ and $\Delta D_{m,i}$ are calculated according to ISO 6976 or GPA 2172 (or any another standard for calculating the Heating Value, Density and Compressibility from the fuel composition at base conditions). Compositions for which the above limits are exceeded, are not taken into account for the next step.

3. The new composition $\psi_H$ is defined by the smallest value for $\Delta HV_{m,i}$ for the $2^{(N-2)}$ hypothetical compositions. From here, $2^{(N-2)}$ new compositions are created in the same manner as described in step 1, with $\psi_H$ used as the new initial composition.

4. This process is repeated until $\Delta HV_{m,i}<0.01$.

5. From the composition defined in this way, the compressibility at base conditions Zbase is determined using the methods of ISO 6976 or GPA 2172 (or another standard for calculating the Heating Value, Density and Compressibility from the fuel composition at base conditions).

6. The real molar Heating Value of the gas is then defined by:

$$HV_{m,r}=HV_{m,i}/Z_{base}.$$

As a result, $HV_{real}$ was determined to be 42.215 MJ/m³.

Determination of Real Molar Velocity of Sound ($VOS_{m,r}$)

Starting from the final gas composition calculated in the previous step, an iteration is applied that gradually changes the composition of the different components such that $VOS_{m,r}$ (the real molar Velocity of Sound) calculated from this composition, converges with the measured $VOS_{m,r}$ value. The iteration is guided by certain limits for $\Delta HV_{m,r}$ and $\Delta D_{m,r}$.

1. Starting from the gas composition calculated by algorithm 1, $\psi_0$, $2^{(n-3)}$ compositions are proposed per iteration step. Each composition differs from each other by the concentration of only one component, which is equal to $\pm(\Delta*C_{i,j})$, with "$\Delta$" a certain step value, and $C_{i,j}$ the concentration of component of the hypothetical composition j.

2. For each composition, $\Delta HV_{m,r}$ and $\Delta D_{m,r}$ are calculated using the equation of state defined by AGA-8 (or any another standard for calculating the real Heating Value, Density and Compressibility from the fuel composition at a defined set of pressure and temperature, for example ISO 6976 or GPA 2172). Compositions for which the above limits are exceeded, are not taken into account for the next step.

3. The new composition $\psi_H$ is defined by the smallest value for $\Delta VOS_{m,r}$ for the $2^{(n-3)}$ hypothetical compositions. From here, $2^{(n-3)}$ new compositions are created in the same manner as described in step 1, with $\psi_H$ used as the new initial composition.

4. This process is repeated until $\Delta VOS_{m,r}<0.002$.

5. The real molar Relative Density of the hydrocarbon fuel is then defined by:

$$RD_{m,r}=AGA8(\psi_H)$$

or any another standard for calculating the real Relative Density from the fuel composition at a defined set of pressure and temperature.

As a result, $RD_{m,r}$ was determined to be 0.6711.

The final composition calculated in the final iteration of the above determination of $RD_{m,r}$ may be used as the starting composition in a re-calculation of both the $HV_{m,r}$ and the $RD_{m,r}$ to further improve the accuracy of the final results. In this manner, these values may be determined to an accuracy greater than 99.95% and 99.9% respectively.

What is claimed is:

1. A method for determining die heating value of a fuel, the fuel comprising at least one hydrocarbon including a first hydrocarbon present in the highest molar concentration, the method comprising:
    measuring the stoichiometric oxidation molar flow ratio of the fuel;
    determining the ideal molar heating value ($HV_{m,i}$) from the measured stoichiometric oxidation molar flow ratio;
    measuring the molar concentration of the first hydrocarbon; and determining the real molar heating value ($HV_{m,r}$) from the ideal molar heating value ($HV_{m,i}$) and the molar concentration of the first hydrocarbon.

2. The method according to claim 1, wherein the fuel is selected from the group consisting of a normally gaseous fuel, generic natural gas, refinery gas, treated natural gas, synthetic natural gas, biogas a liquid fuel, and a lighter crude fraction (class A), liquefied petroleum gas (LPG), gasoline, diesel, kerosene, jet fuel or heating oil.

3. The method according to claim 1, wherein the first hydrocarbon is selected from the group consisting of methane, a higher hydrocarbon, propane and butane.

4. The method according to claim 1, wherein the stoichiometric oxidation molar flow ratio of the fuel is determined by a method selected from the group consisting of measuring the peak temperature of combustion of the fuel and by measurement of the oxygen or air concentration of the fuel gas after combustion.

5. The method according to claim 1, wherein the ideal molar heating value ($HV_{m,i}$) is determined from the measured stoichiometric oxidation molar flow ratio using a relationship between heat value and molar flow ratio.

6. The method according to claim 1, wherein the molar concentration of the first hydrocarbon is determined using non-dispersive infrared (NDIR), gas chromatography, or mass spectroscopy.

7. The method according to claim 1, wherein the molar concentration of the first hydrocarbon is determined to an accuracy of at least +/−2% full scale, more preferably greater than +/−1% full scale.

8. The method according to claim 1, wherein the real molar heating value ($HV_{m,r}$) is determined from the ideal molar heating value ($HV_{m,i}$) and molar concentration of the first hydrocarbon by the following steps:
  i. Determine the correlation factor $R^2$ between $HV_{m,i}$ and the stoichiometric oxidation molar flow ratio for the range of fuels which are to be measured;
  ii. Measure the ideal molar density ($D_{m,i}$) for the fuel to be measured;
  iii. Determine the correlation factor $R^2$ between the ideal molar density ($D_{m,i}$) and the stoichiometric oxidation molar flow ratio for the range of fuels to be measured;
  iv. Define a start composition of the fuel which needs to be measured, with the measured concentration of the first hydrocarbon as a fixed value;
  v. Calculate the $HV_{m,i}$ and $D_{m,i}$;
  vi. Vary the concentration of each component in the start composition in turn, by a small increment to provide a new composition;
  vii. Calculate the $HV_{m,i}$ and $D_{m,i}$ for the new composition;
  viii. Compare the values of $HV_{m,i}$ and $D_{m,i}$ calculated with those derived from the correlation with the stoichiometric oxidation molar flow ratio using the correlation factors $R^2$ for each;
  ix. If the difference in the value of $HV_{m,i}$ between that calculated using the composition and that determined using the correlation factors $R^2$ is less than 0.01%, use the composition to calculate the compressibility of the fuel. If not, repeat steps vi to viii;
  x. Calculate $HV_{m,r}$ by dividing the value of $HV_{m,i}$ for the final composition as obtained from the stoichiometric oxidation molar flow ratio using the correlation factors $R^2$ by the compressibility.

9. An apparatus for determining the heating value of a fuel, the fuel comprising at least one hydrocarbon including a first hydrocarbon present in the highest molar concentration, the apparatus comprising:
  means for measuring the stoichiometric oxidation molar flow ratio of the fuel;
  means for determining the ideal molar heating value ($HV_{m,i}$) from the measured stoichiometric oxidation molar flow ratio;
  means for measuring the molar concentration of the first hydrocarbon; and
  means for determining the real molar heating value ($HV_{m,r}$) from the ideal molar heating value ($HV_{m,i}$) and the molar concentration of the first hydrocarbon.

10. An apparatus for determining the relative density of a fuel comprising at least one hydrocarbon component, the apparatus comprising:
  means for determining the real heating value of the fuel;
  means for measuring the velocity of sound within the fuel;
  means for measuring the concentration of carbon dioxide in the fuel; and
  means for determining the relative density of the fuel from the real heating value, the velocity of sound and the concentration of carbon dioxide.

11. An apparatus for determining the stoichiometric molar ratio of oxygen (or air)/fuel for a hydrocarbon fuel, the apparatus comprising a substrate of inert material having formed therein: a cavity to serve as an oxidation reactor; a conduit for the passage of the fuel from an inlet to the cavity; and a conduit for the passage of oxygen (or air) from an inlet to the cavity.

12. The apparatus according to claim 11, wherein the apparatus is a MEMS device.

13. The apparatus according to claim 11, further comprising a mixer disposed at the inlet to the cavity.

14. The apparatus according to claim 11, wherein the cavity is empty.

15. The apparatus according to claim 11, wherein the cavity contains a catalyst composition.

16. The apparatus according to claim 11, wherein the inert substrate is silicon or glass.

17. The apparatus according to claim 11, wherein the cavity has a volume of less than 1 ml, preferably less than 500 µl, more preferably about 1 µl or less.

18. The apparatus according to claim 11, further comprising a temperature sensor formed within or on the substrate to measure the temperature of the interior of the cavity.

19. The apparatus according to claim 11, further comprising one or more heaters to pre-heat fluids in the conduits.

20. The apparatus according to claim 11, further comprising means to vary the flowrate of fluids through the conduits.

21. The apparatus according to claim 11, wherein each conduit comprises a plurality of conduit channels, the conduit channels of a given conduit having orifice sections of different cross-sectional areas, to provide a range of fluid flow rates through the conduit under conditions of constant pressure.

22. The apparatus according to claim 11, wherein each conduit is provided with a mass flow controller.

23. A method of determining the stoichiometric oxidation ratio for a fuel, the method comprising the steps of:
  providing a reactor for conducting the oxidation of the fuel with oxygen (or air);
  supplying oxygen (or air) to the reactor; supplying the fuel to the reactor;
  maintaining the flow rate of one of the fuel and oxygen (or air) to the reactor constant;
  varying the flow rate of the other of the fuel and oxygen (or air) to the reactor, in order to vary the molar ratio of the fuel and oxygen (or air) being reacted;
  measuring the temperature of the oxidation reaction or the oxygen (or air) concentration at the outlet of the combustion cavity over a range of molar ratios; and
  determining the stoichiometric oxidation ratio from the peak temperature or the oxygen (or air) concentration at the outlet of the combustion cavity.

24. An apparatus for determining the stoichiometric molar flow ratio for oxidation of a fuel, comprising a substrate of inert material the substrate having formed therein:
- a first inlet for the fuel;
- a second inlet for oxygen (or air);
- an outlet for reacted fluid; and
- a plurality of reactor assembles, each reaction assembly comprising:
  - a cavity;
  - a first conduit extending between the cavity and the first inlet for passage of the fuel to the cavity;
  - a second conduit extending between the cavity and the second inlet for passage of oxygen (or air) to the cavity;
  - an outlet conduit extending between the cavity and the outlet; and
  - a temperature sensor for measuring the temperature of fluids reacting within the oxidation cavity, or a sensor to measure the oxygen (or air) concentration at the outlet of the oxidation cavity; wherein each reactor assembly is arranged to provide the fuel and oxygen (or air) to the cavity in a different predetermined molar ratio, wherein the stoichiometric oxidation molar flow ratio is determined from the measured temperatures and the predetermined molar ratios.

25. The apparatus according to claim 24, wherein the apparatus is a MEMS device.

26. The apparatus according to claim 24, comprising at least 4, more preferably at least 10 reactor assemblies arranged in parallel.

27. The apparatus according to claim 24, further comprising means for measuring the concentration of the first hydrocarbon in the fuel.

28. The apparatus according to claim 24, further comprising means for measuring the velocity of sound in the fuel.

29. A method for determining the stoichiometric molar flow ratio for oxidation of a fuel, the method comprising:
- providing a plurality of reactor assemblies, each reaction assembly comprising:
  - an oxidation cavity;
  - a first conduit for passage of the fuel to the cavity; and
  - a second conduit for passage of oxygen (or air) to the cavity; wherein each reactor assembly is arranged to provide the fuel and oxygen (or air) to the cavity in a different predetermined molar ratio;
- supplying fuel to the first conduit of each reactor assembly;
- supplying oxygen (or air) to the second conduit of each reactor assembly;
- controlling the molar flowrate of fluid in each conduit with an internal orifice;
- allowing oxidation of the fuel to occur in each cavity;
- measuring the temperature of oxidation in each cavity, or the oxygen (or air) concentration at the outlet of the cavity; and
- determining the stoichiometric oxidation molar flow ratio from the measured temperatures and the predetermined molar flow ratios.

30. The method according to claim 29, comprising providing at least 4 parallel reactor assemblies, more preferably at least 10 parallel reactor assemblies.

31. The method according to claim 29, further comprising measuring the concentration of the first hydrocarbon.

32. The method according to claim 29, further comprising measuring the velocity of sound in the fuel.

* * * * *